(12) United States Patent
Crofford

(10) Patent No.: US 7,104,995 B2
(45) Date of Patent: Sep. 12, 2006

(54) METHOD OF PREPARING AN ACETABULUM FOR RECEIVING A HEAD OF A FEMORAL PROSTHESIS

(76) Inventor: Theodore W. Crofford, 6863 Lahontan Dr., Fort Worth, TX (US) 76132

( * ) Notice: Subject to any disclaimer, the term of this patent is extended or adjusted under 35 U.S.C. 154(b) by 0 days.

(21) Appl. No.: 10/914,750

(22) Filed: Aug. 9, 2004

(65) Prior Publication Data

US 2005/0010230 A1    Jan. 13, 2005

Related U.S. Application Data

(63) Continuation-in-part of application No. 10/779,353, filed on Feb. 14, 2004, which is a continuation of application No. 10/228,907, filed on Aug. 27, 2002, now Pat. No. 6,695,883.

(60) Provisional application No. 60/371,837, filed on Apr. 11, 2002.

(51) Int. Cl.
    A61B 17/00    (2006.01)
(52) U.S. Cl. ............................................. 606/81
(58) Field of Classification Search .............. 606/72, 606/89, 96, 99, 81; 623/23.11–12, 23.14, 623/23.26–27
    See application file for complete search history.

(56) References Cited

U.S. PATENT DOCUMENTS

| | | | |
|---|---|---|---|
| 4,005,495 A | | 2/1977 | Locke et al. |
| 4,129,903 A | * | 12/1978 | Huggler .................... 623/23.11 |
| 4,224,699 A | | 9/1980 | Weber |
| 4,795,473 A | * | 1/1989 | Grimes .................... 623/23.11 |
| 4,976,740 A | | 12/1990 | Kleiner |
| 4,998,937 A | * | 3/1991 | Grimes ........................ 606/89 |
| 5,035,717 A | | 7/1991 | Brooks |
| 5,133,760 A | | 7/1992 | Petersen et al. |
| 5,147,403 A | | 9/1992 | Gitelis |
| 5,318,571 A | | 6/1994 | Benson |
| 5,320,625 A | * | 6/1994 | Bertin .......................... 606/91 |
| 5,342,363 A | * | 8/1994 | Richelsoph .................. 606/79 |
| 5,376,125 A | | 12/1994 | Winkler |
| 5,571,203 A | | 11/1996 | Masini |
| 5,741,262 A | * | 4/1998 | Albrektsson et al. .......... 606/80 |
| 5,800,553 A | * | 9/1998 | Albrektsson et al. ....... 623/22.4 |
| 5,976,148 A | * | 11/1999 | Charpenet et al. ............ 606/91 |

(Continued)

FOREIGN PATENT DOCUMENTS

DE    197 25 269 A    1/1999

(Continued)

OTHER PUBLICATIONS

PCT International Search Report Jul. 30, 2003, Crofford.

(Continued)

*Primary Examiner*—Eduardo C. Robert
*Assistant Examiner*—Annette Reimers
(74) *Attorney, Agent, or Firm*—Patton Boggs LLP

(57) ABSTRACT

A femoral neck fixation prosthesis and method of using same which reduces bone loss and the avoids the other shortcomings of the prior art by allowing the fixation of a stable femoral head replacement while reducing the amount of the femur which must be reamed for the insertion of the prosthesis. The preferred embodiment provides that the femoral head is attached to a fixation prosthesis, which extends coaxially through the canal of the femoral neck, into the femur, and is then attached to the opposite lateral wall of the femur. In this manner, the prosthesis serves to imitate the original structure of the femoral neck. No other support members, either crosspins or arms extending into the length of the femur, are required.

4 Claims, 19 Drawing Sheets

U.S. PATENT DOCUMENTS

| | | | |
|---|---|---|---|
| 5,980,575 A * | 11/1999 | Albrektsson et al. | 623/23.11 |
| 6,120,510 A * | 9/2000 | Albrektsson et al. | 606/96 |
| 6,231,611 B1 * | 5/2001 | Mosseri | 623/22.12 |
| 6,273,915 B1 * | 8/2001 | Grimes | 623/23.21 |
| 6,284,002 B1 * | 9/2001 | Sotereanos | 623/27 |
| 6,379,390 B1 | 4/2002 | Advani et al. | |
| 6,383,227 B1 * | 5/2002 | Baroud et al. | 623/23.22 |
| 6,482,237 B1 * | 11/2002 | Mosseri | 623/22.12 |
| 6,508,841 B1 | 1/2003 | Martin et al. | |
| 6,616,697 B1 * | 9/2003 | Sotereanos | 623/23.26 |
| 6,706,073 B1 * | 3/2004 | Draenert et al. | 623/22.46 |
| 6,723,102 B1 * | 4/2004 | Johnson et al. | 606/79 |
| 6,770,100 B1 | 8/2004 | Draenert | |
| 2002/0095217 A1 | 7/2002 | Masini | |
| 2002/0143402 A1 * | 10/2002 | Steinberg | 623/22.16 |
| 2005/0049712 A1 | 3/2005 | Ondria et al. | |

FOREIGN PATENT DOCUMENTS

| | | |
|---|---|---|
| DE | 198 34 277 A | 2/2000 |
| EP | 0 099 167 A | 1/1984 |
| EP | 0 791 342 A | 8/1997 |
| FR | 1 075 914 A | 10/1954 |
| GB | 2 033 755 A | 5/1980 |
| WO | WO 86/03962 | 7/1986 |
| WO | WO 89/11837 | 12/1989 |
| WO | WO 93/16663 | 9/1993 |
| WO | WO 97/25939 | 7/1997 |

OTHER PUBLICATIONS

Harlan C. Amstutz, MD and Peter Grigoris, MD, PhD; Metal on Metal Bearings in Hip Arthroplasty; Clinical Orthopaedics and Related Research, 1996, No. 329S; pp. S11-S34.

A.H. Huggler, and H.A.C. Jacob (Eds.); The Thrust Plate Hip Prosthesis; Springer-Verlag Berlin Heidelberg 1997; 3 pages submitted.

Tomas Albrektsson, MD, PhD, Lars V. Carlsson, MD, PhD, Magnus Jacobsson, MD, PhD, and Warren MacDonald, CEng, MPhil; Clinical Orthopaedics and Related Research, 1998, No. 352; pp. 81-94.

Prof. Dr. A.H. Huggler and Dr. Ing. H.A.C. Jacob; The Thrust Plate Process; All Pro; Jan. 1993, 16 pages.

H. Bereiter, A.H. Huggler. H.A.C. Jacob, and P. Seemann; The Thrust Plate Prosthesis (TPP) A New Concept in Hip Prosthesis Design Eight Years of Clinical Experience; Orthop Rel. Sci. 2, Date Unknown; pp. 191-202.

A.H. Huggler and H.A.C. Jacob; The Uncemented Thrust-Pate Hip Prosthesis; Date Unknown; pp. 125-129.

European Search Report dated Jul. 15, 2005.

PCT International Search Report dated Nov. 25, 2005.

* cited by examiner

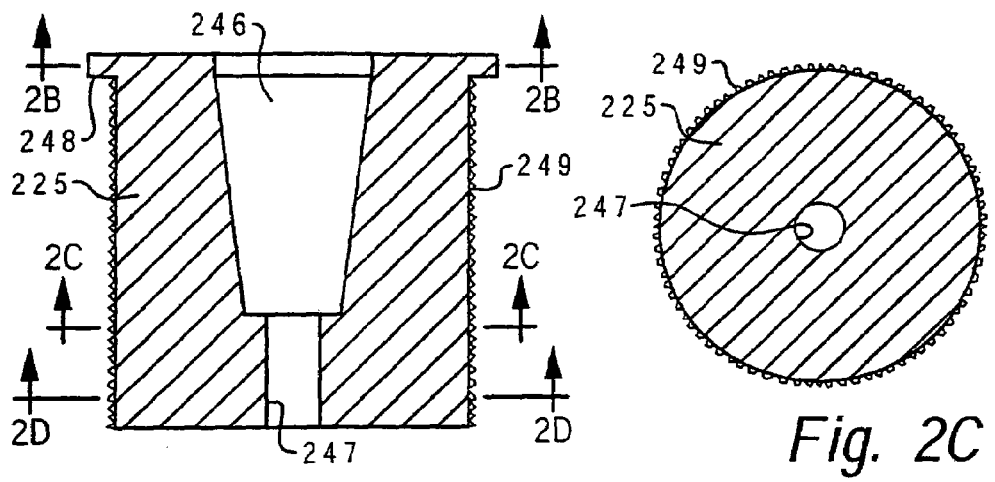
Fig. 2A
Fig. 2C
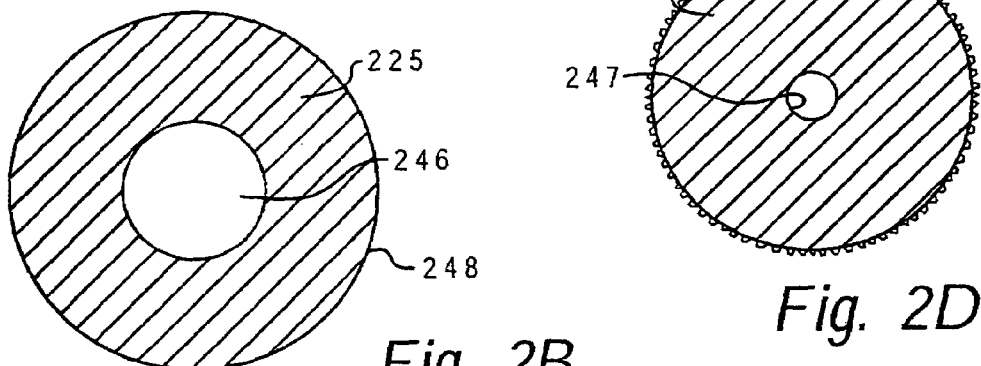
Fig. 2B
Fig. 2D
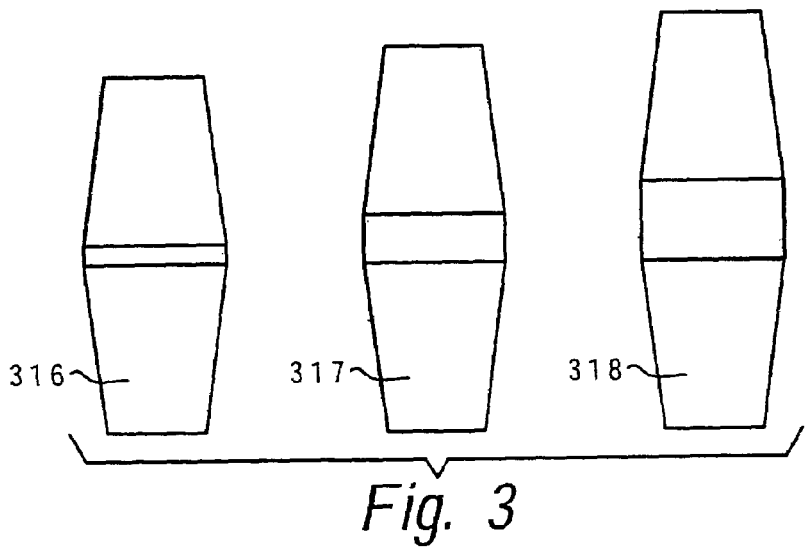
Fig. 3

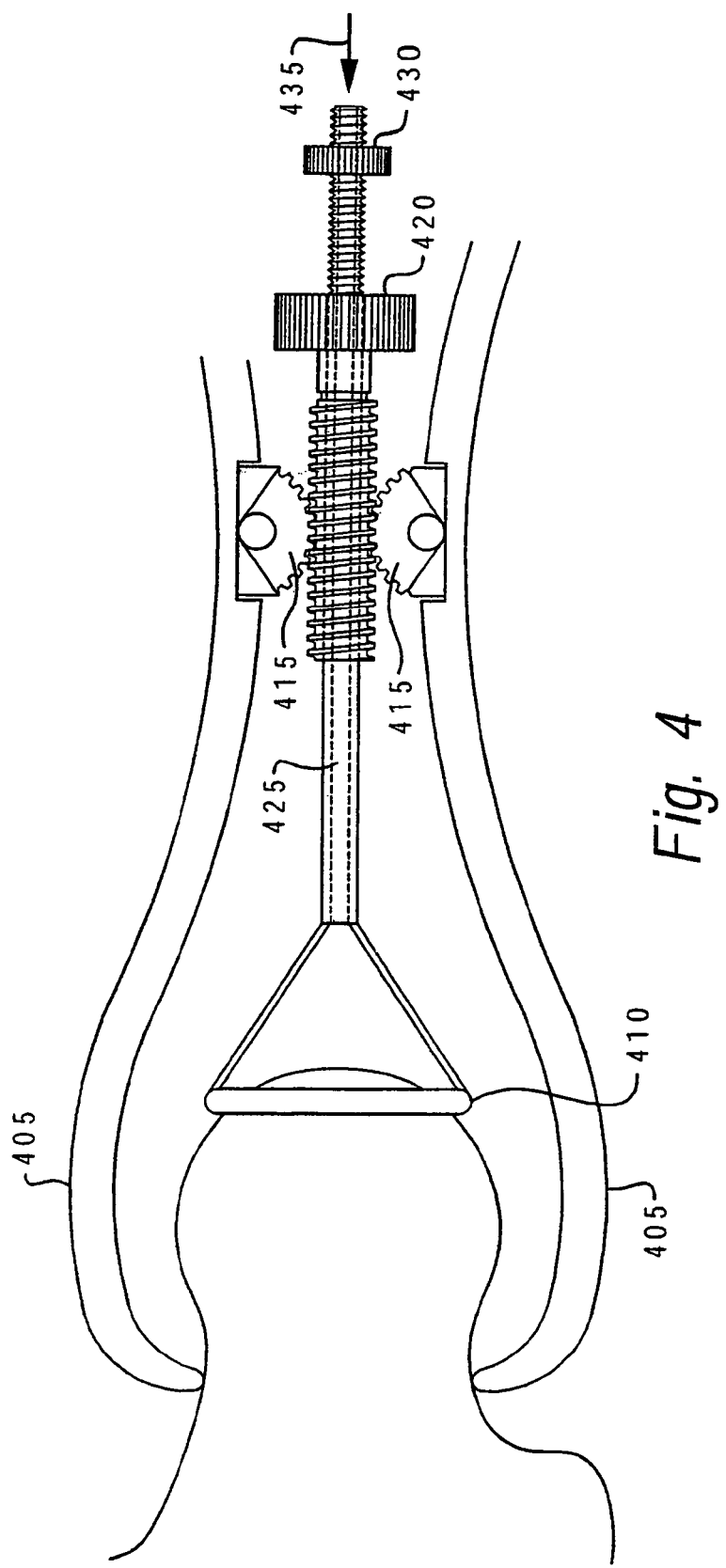

METHOD OF PREPARING AN ACETABULUM FOR RECEIVING A HEAD OF A FEMORAL PROSTHESIS

CROSS-REFERENCE TO RELATED APPLICATIONS

This application is a continuation-in-part of and claims priority to U.S. patent application Ser. No. 10/779,353, filed Feb. 14, 2004, which is a continuation of U.S. patent application Ser. No. 10/228,907, filed Aug. 27, 2002, now U.S. Pat. No. 6,695,883, which claims priority to U.S. Provisional Application No. 60/371,837, filed Apr. 11, 2002. Priority is claimed to all of the above-mentioned applications and patents, and each application and patent is hereby incorporated by reference.

BACKGROUND OF THE INVENTION

1. Field of the Invention

The present application relates generally to hip prostheses and more specifically to an improved method of implanting a femoral neck fixation prosthesis in the femoral neck.

2. Description of Related Art

A widely used design for replacement of the proximal portion of a femur employs an elongate, often curved, shaft that extends into the medullary canal of the femur. This design has the tendency to place unnatural stresses on the femur, which lead to pain and the consequent curtailment of activity for the patient. Further, present techniques can lead to proximal bone loss and call for the resection of the majority of the femoral neck. Current designs also call for fixing the prosthesis in the proximal third of the femur. The useful life of an intramedullary implant is often less than the expected life span of a young patient.

Previously known prostheses for replacing a femoral head that do not extend into the medullary canal have been mechanically complex or have proven troublesome in actual use. Huggler, U.S. Pat. No. 4,129,903 and Grimes, U.S. Pat. No. 4,795,473 are examples of prosthetic implants having a side plate attached to the exterior lateral side of the femur opposite the femoral head. Screws are used to secure the plate to the femur and one or more holes are drilled into the femur for securing the plate to the bone. The additional holes and the stresses at the site of fixation are believed to cause trauma to the bone.

Masini, U.S. Pat. No. 5,571,203 discloses a device having a shaft that extends through a resected portion of the proximal femur, positioned co-axially relative to the longitudinal axis of the femur. The device is secured by a screw or similar locking device that extends into the femur from the lateral side, just below the greater trochanter. It is believed that the natural forces applied to the prosthesis during normal hip motion result in the application of shear forces to the greater trochanter. The shear forces can be harmful to the greater trochanter and can permit micro-movement of the prosthesis on the unsecured side.

A conventional method for implanting the above types of femoral head implants is described in Campbell's Operative Orthopaedics, (Mosby, 7th ed., 1987) and typically includes making a large incision in the patient's lateral side at the hip joint and through the skin and muscle, dislocating the hip and then sawing off the femoral head. This method is considered invasive because of the need to dislocate the hip and cut through muscle surrounding the hip joint. Invasive procedures increase the trauma to the patient, the potential for complications, recovery time and the cost.

Replacement of the proximal portion of the femur is sometimes necessary due to degenerative bone disorders or trauma to otherwise healthy bone caused by accidental injury. In the latter instance it is desirable to replace the traumatized portion of the bone without causing further trauma to healthy bone. There is a need, therefore, for an implant that replaces a traumatized portion of the femur, but also significantly minimizes stress to the remaining healthy bone and that can be implanted by a method that is less invasive.

There are several other significant problems and issues relating to hip arthroplasty. One problem is encountered with the young, active patient. Younger patients are more likely to have failure of their primary arthroplasty both due to increased demand on the mechanical construct, and from a pure life expectancy standpoint. It follows that they are more likely to require a revision and a second revision, which may lead to a catastrophic bone loss situation.

Another problem relates to instability of the hip following implantation of the prosthesis. This problem still occurs at the same rate that it did 50 years ago. Larger femoral heads may decrease the incidence, but no other significant technical changes have occurred to effect the incidence of this serious complication.

Still another problem is related to bone loss in patients receiving hip prostheses. The overwhelming majority of present successful femoral prostheses achieve fixation at least as far distal as the proximal femoral metaphysis. When these prostheses fail, the next step usually involves diaphyseal fixation, often with a large diameter, stiff stem.

Leg length inequality is another problem associated with hip arthroplasty. An average lengthening of the leg of 1 centimeter is common. Lengthening is sometimes accepted for the sake of improved stability; however, leg length inequality has been reported as the primary reason why surgeons are sued after hip arthroplasty.

Finally, another problem associated with hip arthroplasty is surgical morbidity. The surgery usually involves significant blood loss, body fluid alterations, and pain. Shortly, the surgery is a big operation that hurts. It should be the goal of every compassionate surgeon to minimize these issues. If the operation can be made smaller, with less blood loss and less pain without diminishing long term results, every effort should be made to do so.

It would therefore be desirable to provide a femoral neck prosthesis and method for implanting the prosthesis that overcomes these significant disadvantages.

BRIEF SUMMARY OF THE INVENTION

It is therefore one object of the present invention to provide an improved apparatus and method for hip replacements.

It is another object of the present invention to provide an improved and less-invasive prosthesis and implantation method that replaces the femoral head while retaining a substantially intact femoral neck.

The foregoing objects are achieved as is now described. A femoral neck fixation prosthesis and method of implanting the prosthesis according to the principles of the present invention, reduce bone loss and avoid the other shortcomings of the prior art by allowing the fixation of a stable femoral head replacement while reducing the amount of the femur that must be removed and reamed for the insertion of the prosthesis. The preferred embodiment provides that the femoral head is attached to a fixation prosthesis, which extends coaxially through the central canal of the femoral neck, into the femur, and is then attached to the opposite lateral wall of the femur. In this manner, the prosthesis serves to imitate the original structure of the femoral neck. No other support members, either crosspins or arms extending into the length of the femur, are required.

The above as well as additional objectives, features, and advantages of the present invention will become apparent in the following detailed written description.

BRIEF DESCRIPTION OF THE DRAWINGS

FIGS. 2A–2H depict a schematic of the cross-section at various levels of the body of a prosthesis in accordance with the present invention;

FIG. 3 illustrates joining members used with a prosthesis in accordance with the present invention;

FIG. 4 depicts a centering guide for placement of a starting pin in accordance with the present invention;

DETAILED DESCRIPTION OF THE PREFERRED EMBODIMENT

Figure 1:
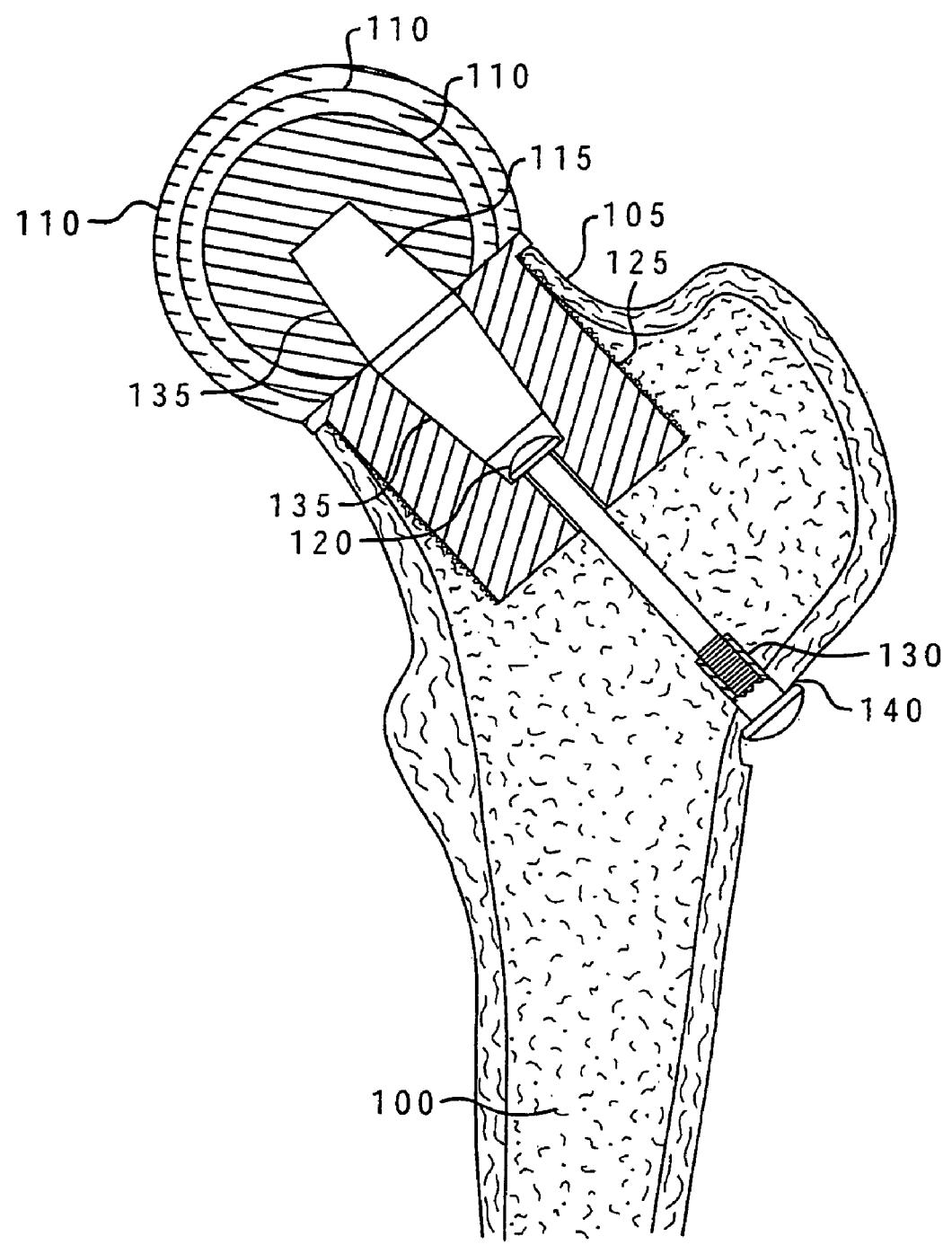
FIG. 1 illustrates a schematic of an anterior view of a prosthesis in accordance with the principles of the present invention.

In the following detailed description of the preferred embodiments, reference is made to the accompanying drawings, which form a part hereof and in which is shown by way of illustration specific preferred embodiments in which the invention may be practiced. These embodiments are described in sufficient detail to enable those skilled in the art to practice the invention, and it is understood that other embodiments may be utilized and that logical mechanical, structural, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The present invention provides a femoral neck fixation prosthesis and a method of implanting the prosthesis which reduces bone loss and avoids the other shortcomings of the prior art by allowing the fixation of a stable femoral head replacement while reducing the amount of the femur, that must be removed and reamed for the insertion of the prosthesis. The preferred embodiment provides that the femoral head is attached to a fixation prosthesis, which extends coaxially through the central canal of the femoral neck, into the femur, and is then attached to the opposite lateral wall of the femur. In this manner, the prosthesis serves to imitate the original structure of the femoral head while substantially retaining the natural femoral neck. No other support members, either crosspins or arms extending into the length of the femur, are required.

A femoral neck fixation prosthesis in accordance with the principles of the present invention is designed to achieve fixation in the femoral neck with or without cement. Therefore, revision of the disclosed femoral neck fixation prosthesis would essentially become the complexity of a present day primary hip arthroplasty for the femoral component. The improved femoral neck fixation prosthesis would require an operation equivalent to a primary arthroplasty on the femoral side. Therefore it would be ideal for the younger patient, but would also be recommended for the older patients with accommodating anatomy.

The innovative method for implanting the femoral neck fixation prosthesis would allow less muscular dissection, and the capsule can be repaired anteriorly at the end of the procedure. The disclosed femoral neck fixation prosthesis is designed to be used with larger diameter femoral heads. The combination of these factors would significantly improve stability of the hip. The goal is to minimize the need for hip position precautions postoperatively.

One advantage of the preferred embodiment is that less bone would be resected initially using the femoral neck fixation prosthesis, and the stress would be transferred to the bone in the femoral neck. The metaphysis and the diaphysis of the proximal femur would be minimally disturbed. Only the femoral head itself will be resected.

Another advantage of the preferred embodiment, is that the femoral neck length and offset would be accurately measured and reproduced when using the femoral neck fixation prosthesis. Leg length inequality due to hip arthroplasty could be minimized, and muscle mechanics could be accurately restored.

Further, an operation using the femoral neck fixation prosthesis would be less invasive with less blood loss, less post operative pain, and less perioperative morbidity than an operation that employs the vast majority of commonly used prostheses. The economic implications of a shorter hospital stay, fewer blood transfusions, and fewer medical complications are significant.

A femoral neck fixation prosthesis according to the principles of the present invention is shown in FIG. 1, wherein femur 100 is shown with femoral neck 105, joining member 115, and prosthetic head 110.

An uncemented porous coated femoral prosthesis body 125 with a modular head 110 and joining member 115 is provided. The metal used is preferably either titanium or chrome-cobalt based, and can be any metal commonly used in hip prosthesis construction. The modulus of elasticity of such a short segment will be of less significance than in a standard femoral stem. The coating is preferably either sintered beads or plasma sprayed, depending on the type of metal used for the body of the prosthesis.

The body 125 of the prosthesis will preferably be available in various diameters, approximately every 1–1.5 mm. The length of the prosthesis will preferably be chosen from one or two lengths, approximately 30 mm. Most of the fixation and ingrowth of the bone to the prosthesis will occur in the first 10–20 mm.

As described in more detail below, fixation to the femur will be achieved by reaming the femoral neck 105 to accommodate a cylindrical porous coated sleeve body 125, which is supported by a proximal collar and given distal stability with a compression screw 120 through the lateral wall of the femur just distal to the greater tuberosity (location 140). Reaming will be progressive until the cortex of the femoral neck is encountered. A femoral component ½ mm greater than the last diameter reamed will then be selected.

After insertion, the long axis of the body of the component body 125 will coincide with a longitudinal axis in the preoperative femur 100 corresponding to an imaginary line connecting the center of the femoral neck 105 with the center of the femoral head 110. Resection of the femoral head will be measured such that the center of rotation of the femoral head 110 can be measured and reproduced. The femoral neck 105 will be reamed with a planar reamer that fits in the reamed canal of the femoral neck 105 to establish a flat surface. The proximal body 125 of the prosthesis will have the female end of a morse taper to allow the attachment of the joining member 115.

A compression screw 120 passes through the center of the body of the prosthesis. This screw attaches to a barrel nut 130 in the lateral wall of the femur at point 140 and preferably has a hexagonal head. The screw 120 is preferably smooth in the segment within the body of the prosthesis and has threads on the distal end. The tunnel through the body of the prosthesis forms a snug fit around the smooth portion of the screw 120. The barrel nut 130 is preferably angled to be flush with the lateral side of the femur at point 140. The head of the screw 120 is preferably located in the base of the morse taper in the body 125 of the femoral component. This screw 120 adds stability to the construct by giving antero-posterior and varus-valgus stability to the body 125 of the prosthesis and by compressing the prosthesis on the neck 105 of the femur 100. These screws will be available in various lengths.

It is important to note that this innovative design allows the prosthesis to be installed and used without requiring any other fastener on the femur. In particular, the preferred embodiment does not require any additional screws or other fasteners to be placed in the femur, and does not require any sort of support plate on the lateral wall of the femur.

Male-male morse taper joining member 115 acts as a joining portion in connecting the body 125 of the prosthesis to the femoral head 110. Adjustments in joining member length will occur in this segment with several lengths of joining member segments available for each femoral body and femoral head. The joining member segment needed to exactly reproduce the center of rotation of the femoral head will be known based on the amount of bone resected. In this embodiment, the joining member 115 has male morse tapers 135 on each side, and will have a variable-length section in between the morse tapers to fit the specific patient.

The femoral head 110 will have a female morse taper to connect to the joining member 115. Femoral heads 110 will be of various diameters depending on the acetabulum, and several exemplary sizes are shown in FIG. 1. Ideally, larger femoral head diameters (e.g., 36 mm to 50 mm) are used to both improve stability and prevent impingement of the neck on the acetabular rim. The femoral head 110 is preferably polished chrome-cobalt, as the industry standard, but other materials can be used.

In another embodiment of the present invention, a de-rotation component is added to reduce the likelihood of the rotation of the prosthesis within the femoral neck. This can be accomplished with a pin or stem with grooves or slots that passes through the lateral cortex into the body of the prosthesis. This would then be compressed with a screw, which would be put through the head end of the body of the prosthesis into the stem.

It should be clear that the femoral neck fixation prostheses described herein can be used with or without cement.

FIGS. 2A–2C show several cross-sectional views of the cylindrical porous coated body 225 of the prosthesis of the preferred embodiment. FIG. 2A shows a longitudinal cross-section of the body 225. In this view, a collar 248 at the proximal end of the body 225 is illustrated, as is the female morse taper cavity 246, which is fit to receive the joining member. The collar 248 is configured to abut the proximal end of the resected femoral neck. Communicating with cavity 246 is tubular channel 247 which will receive the compression screw. Below the collar 248, the exterior of the body 225 has a porous coated layer 249.

Figure 2E:
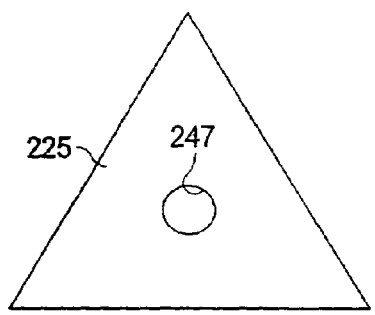
Figure 2F:
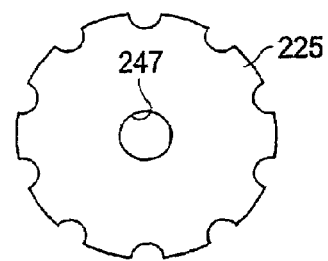
Figure 2G:
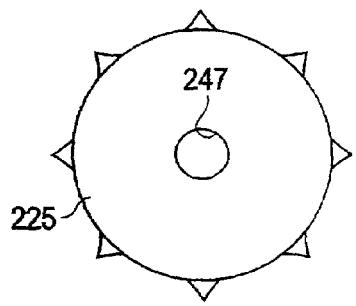
Figure 2H:
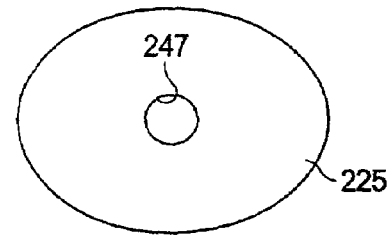

While the preferred embodiment has a substantially circular cross-section, as shown in FIGS. 2A–2C, the body member 225 can also be configured with a triangular (FIG. 2E), scalloped (FIG. 2F), oval (FIG. 2H), or fluted (FIG. 2G) cross-section.

FIG. 2B shows a lateral cross-section of body 225 as cut across line B of FIG. 2A. In FIG. 2B, the cavity 246 is shown, and the proximal collar 248 is also illustrated.

FIG. 2C shows a lateral cross-section of body 225 as cut across line C of FIG. 2A. In FIG. 2C, channel 247 for the compression screw is shown passing through the center of body 225. On the exterior of body 225 is shown the porous coated layer 249. A cross-section across line D of FIG. 2A is the same as described for line C of that FIG.

FIG. 3 shows joining members 316/317/318 of various sizes, which can be used for patients with differing requirements. Each joining member 316/317/318 has a morse taper on each end, and a variable-length straight section connecting the morse tapers.

FIG. 4 depicts the centering guide for placement of the starting pin in accordance with the principles of the present invention. In this FIG., femoral neck gripping clamp 405 is to grip and hold the femoral neck after the femoral head centering device 410 has been placed over the patient's femoral head.

The femoral neck gripping clamp 405 is expanded or contracted using adjustment piece 420, which operates gears 415. Cannulated rod 425, which is connected to femoral head centering device 410, allows pin insertion into the cannula at 435.

Free nut 430 is used to tighten the femoral head centering device 410. The centering guide shown in FIG. 4 is preferably made of a stiff metal, and can also be used as a retractor to expose the femoral head.

Figure 5:
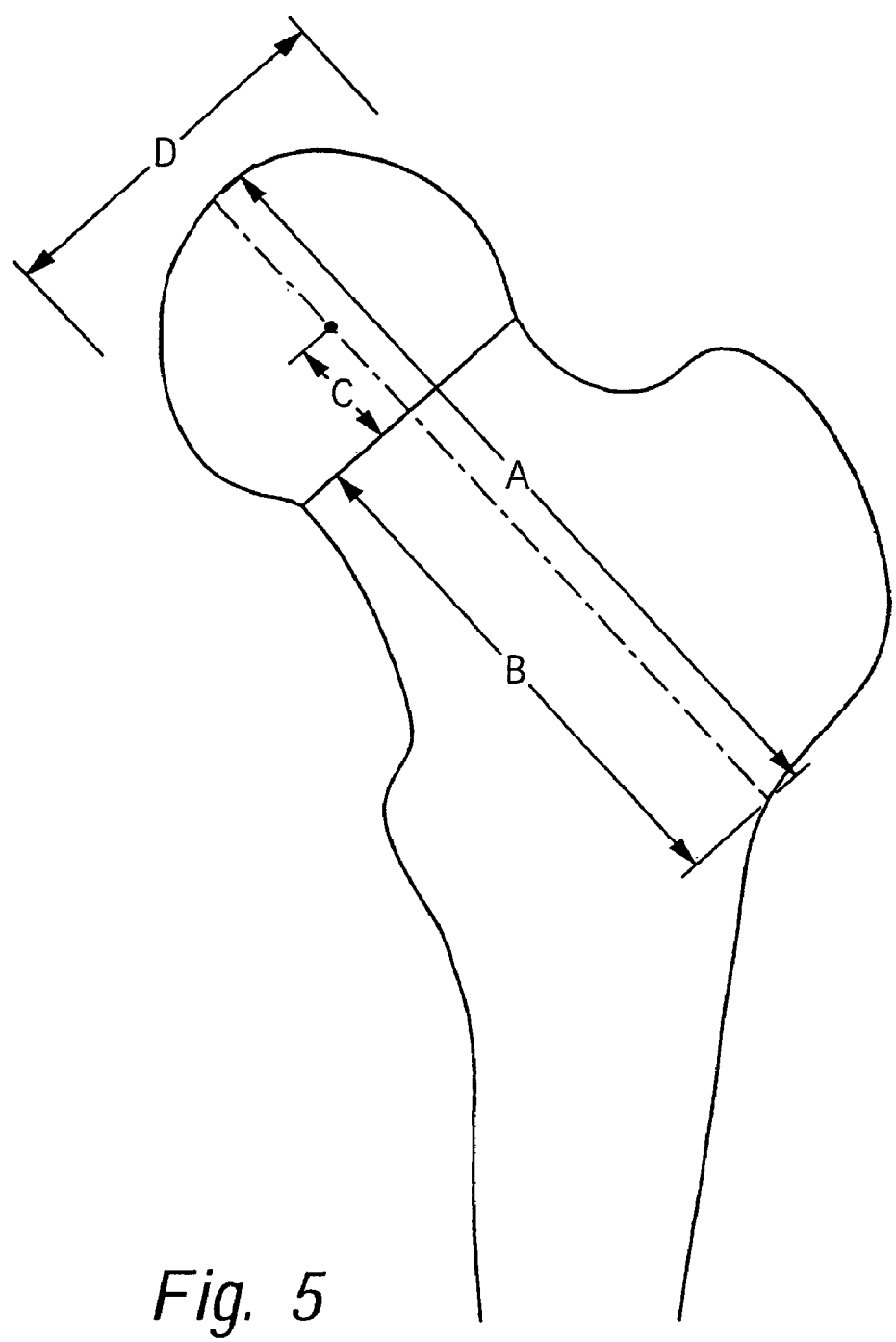
FIG. 5 illustrates how the center of rotation of the femoral head can be reproduced in accordance with the present invention.

FIG. 5 depicts how the center of rotation of the femoral head can be reproduced in accordance with a preferred embodiment of the present invention. First, distance A from the head to the lateral cortex is measured. After the femoral head is removed, distance B, from the cut surface to the lateral cortex, is measured. The diameter D of the femoral head is also measured. When these measurements are known, distance C is calculated using the formula $$C=(A-D/2)-B$$

Distance C then represents the distance from the cut surface of the femoral neck that the prosthetic femoral head center-of-rotation should be placed in order to reproduce the pre-operative femoral head center-of-rotation.

Figure 6:
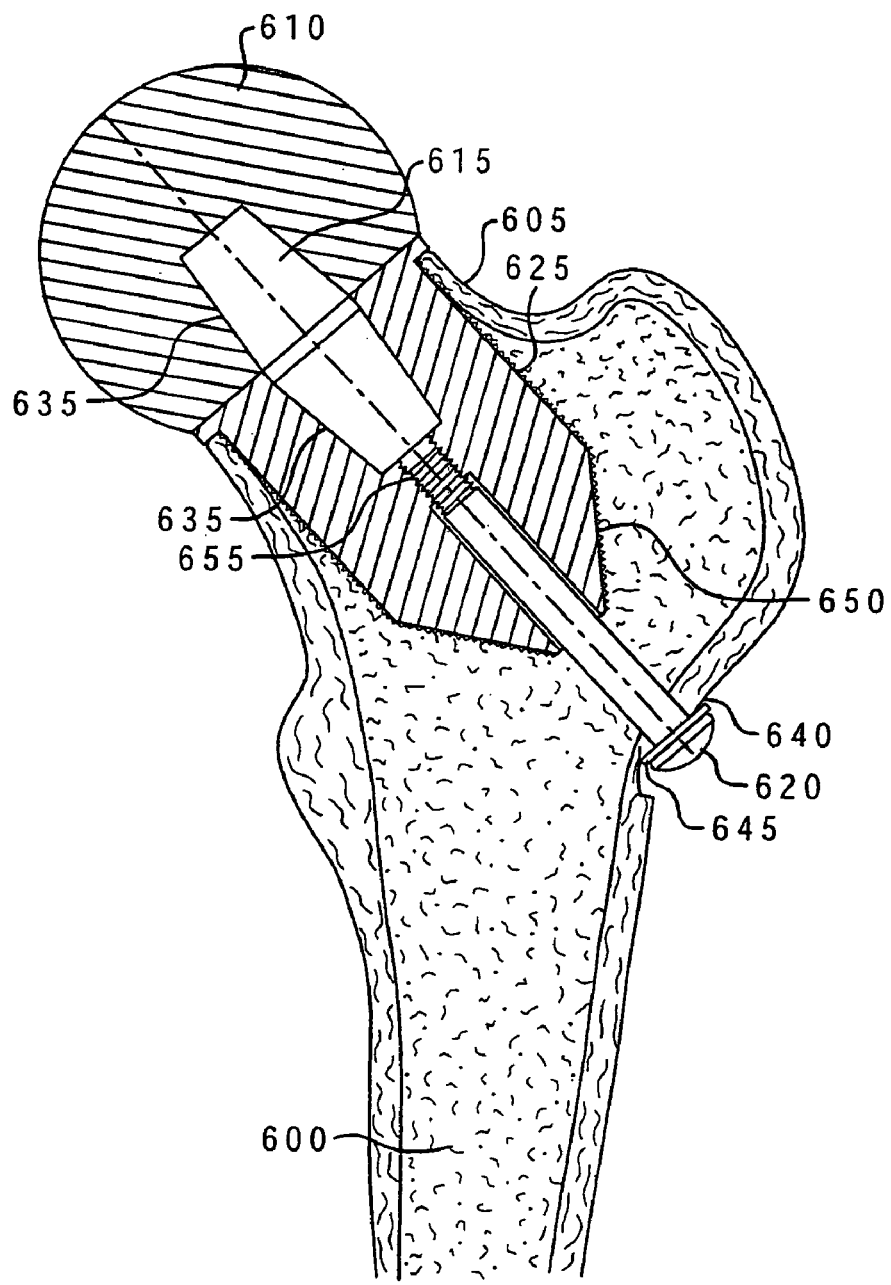
FIG. 6 depicts a prosthesis in accordance with the principles of the present invention.

In another embodiment shown in FIG. 6, compression screw 620, preferably with washer 645, is inserted through the lateral wall of the femur at location 640 and screwed into the body 625 of the femoral component. This simplifies the barrel nut portion of the design shown in FIG. 1. It would require that the screw 620 be of various lengths that would engage the body 625 of the prosthesis without reaching the depth of the hole in the femoral prosthesis. The body of the prosthesis would preferably be longer, using optional extension 650 to provide enough length so that the compression screw will be stable within the body of the prosthesis.

The remainder of FIG. 6 is similar to FIG. 1. In this FIG., femur 600 is shown with femoral neck 605, joining member 615, and prosthetic head 610.

This embodiment provides an uncemented porous coated femoral prosthesis body 625 with a modular head 610 and joining member 615. The body 625 of the prosthesis include threads 655 for receiving screw 620.

As described in more detail below, fixation to the femur will be achieved by reaming the femoral neck 605 to accommodate a cylindrical porous coated sleeve body 625, which is supported by a proximal collar and given distal stability with a compression screw 620 through the lateral wall of the femur just distal to the greater tuberosity (location 640).

After insertion, the long axis of the body of the component body 625 will coincide with a longitudinal axis in the preoperative femur 600 corresponding to an imaginary line connecting the center of the femoral neck 605 with the center of the femoral head 610. Resection of the femoral head will be measured such that the center of rotation of the femoral head 610 can be measured and reproduced as discussed with reference to FIG. 5. The femoral neck 605 will be reamed with a flat reamer that fits in the reamed canal of the femoral neck 605 to establish a flat surface. The proximal body 625 of the prosthesis will have the female end of a morse taper to allow the attachment of the femoral neck 615.

Compression screw 620 passes through the center of the body of the prosthesis. The screw 620 is preferably smooth in the segment within the body of the prosthesis and has threads on the proximal end, for engaging threads 655. The tunnel through the body of the prosthesis forms a snug fit around the smooth portion of the screw 620. Screw 620 adds stability to the construct by giving antero-posterior and varus-valgus stability to the body 625 of the prosthesis and by compressing the prosthesis on the neck 605 of the femur 600. These screws will be available in various lengths.

Male-male morse taper joining member 615 connects the body 625 of the prosthesis to the femoral head 610. Adjustments in joining member neck length will occur in this segment with several lengths of joining member segments available for each femoral body and femoral head. The joining member segment needed to exactly reproduce the center of rotation of the femoral head will be known based on the amount of bone resected.

The femoral head 610 will have a female morse taper to connect to the joining member 615. Femoral heads 610 will be of various diameters depending on the acetabulum. Ideally larger femoral head diameters (e.g., 36 mm to 60 mm) are used to both improve stability and prevent impingement of the neck on the acetabular rim. The femoral head 610 is preferably polished chrome-cobalt, as the industry standard, but other materials can be used.

Figure 7:
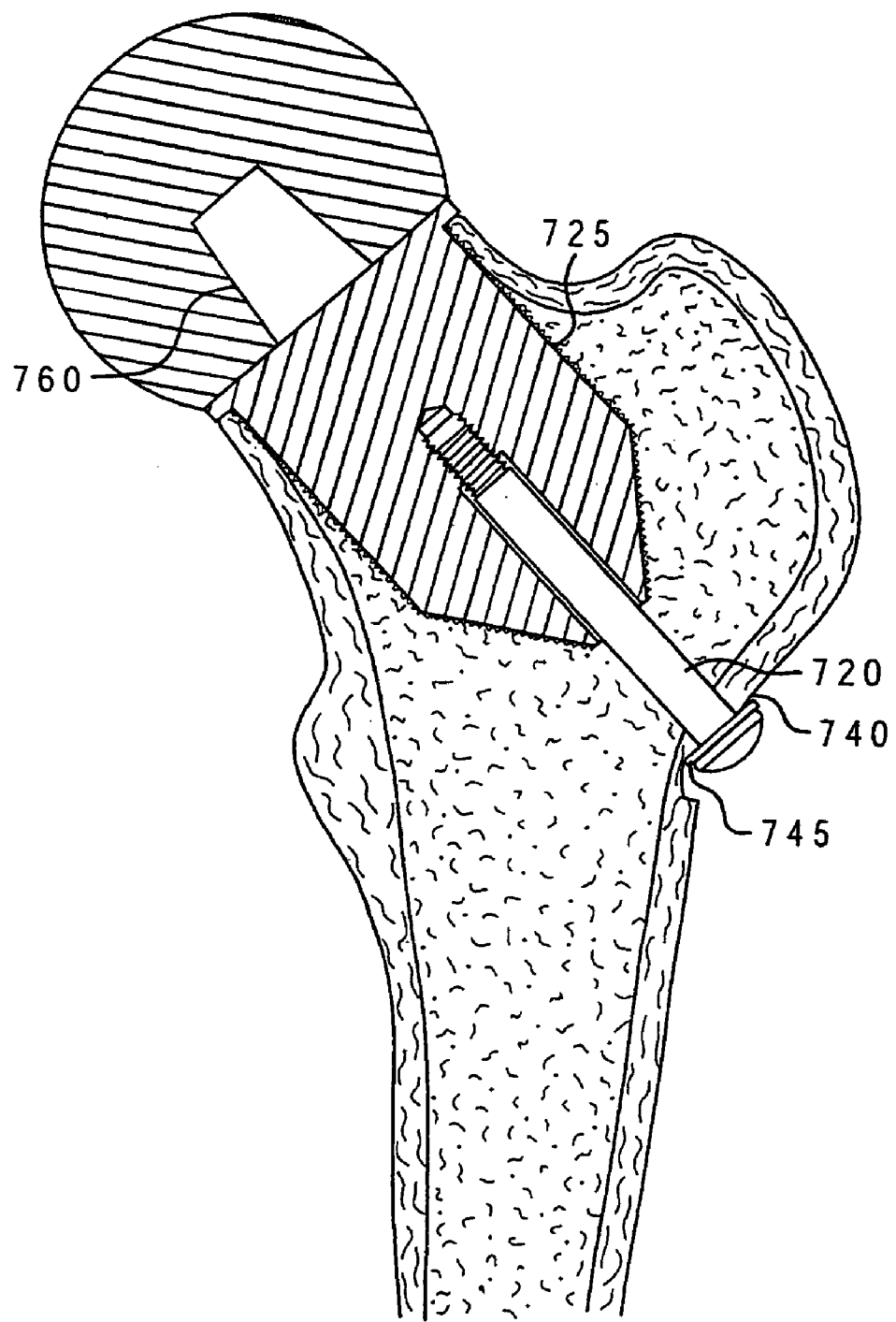
FIG. 7 illustrates a prosthesis in accordance with the principles of the present invention.

FIG. 7 shows a preferred embodiment of the femoral neck fixation prosthesis of the present invention. If the compression screw 720, with washer 745, is inserted through the lateral wall of the femur at 740, the length of the body 725 of the prosthesis may not be long enough to provide adequate stability for the compression screw 720. In order to provide this stability for the compression screw, a fixed length joining member 760 on the body of the prosthesis would be necessary to act as a joining member, abandoning the modular joining member (115 in FIG. 1). The varied lengths required on the joining member would be incorporated into the femoral head either with separate individual lengths for each head diameter (2 to 3 for each diameter femoral head) or by using an interposing piece of metal to provide additional neck length. The latter is done with several femoral components available on the market today.

Figure 8:
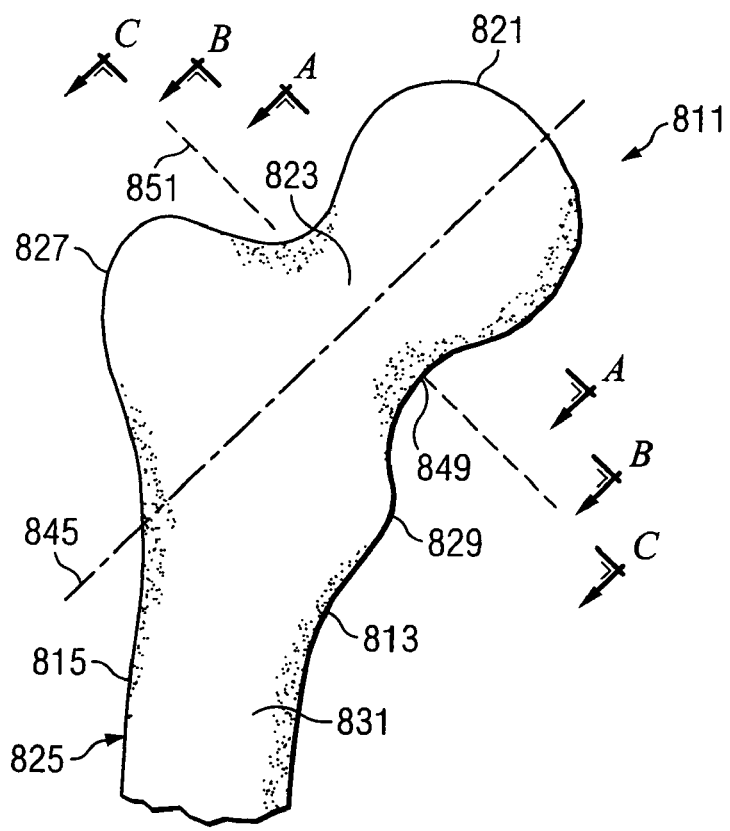
FIG. 8 depicts a posterior view of a human femur having a femoral head and a femoral neck.

The femoral neck fixation prosthesis is implanted by first preparing the femur for reception of the prosthesis. Referring to FIG. 8, several orientations and anatomical features relative to a femur 811 should first be defined to more easily understand the process of preparing the femur and implanting the prosthesis. As used herein, the term "medial" shall mean "pertaining to the middle," while the term "lateral" shall mean "pertaining to the side." The femur 811 includes a medial side 813 and a lateral side 815. The term "proximal" shall mean "nearest the point of attachment, center of the body, or point of reference," while the term "distal" shall mean "the opposite of proximal, or farthest from the center, from a medial line, or from the trunk." The terms proximal and distal are generally used to convey positional or directional information relative to a particular feature, so it would not be entirely proper to refer to a proximal "side" of the femur or a distal "side" of the femur. However, these terms can be demonstrated by comparing some of the basic anatomy of the femur. Femur 811 includes a femoral head 821, a femoral neck 823, a shaft 825, a greater trochanter 827, and a lesser trochanter 829. Since the femoral head 811 serves as a point of attachment when it is received by the acetabulum (not shown), the femoral head 821 is located proximal to the femoral neck 823 and the shaft 825. The shaft 825 is located distal to both the femoral neck 823 and the femoral head 821. As used herein the term "superior" shall mean "higher than or situated above something else," while the term "inferior" shall mean "beneath or lower." The term "anterior" shall mean "before or in front of" and shall generally refer to the ventral or abdominal side of the body. The term "posterior" shall mean "toward the rear" and shall generally refer to the back or dorsal side of the body. A posterior side 831 of the femur 811 is shown in FIG. 8, while the anterior side is hidden from view in FIG. 8.

A longitudinal axis 845 of the femoral neck is difficult to precisely define because the geometry of the femoral neck 823 is usually not perfectly cylindrical. Theoretically speaking, if the femoral neck 823 were sectioned along its length at a finite number of cross-sectional planes (e.g. B—B and C—C in FIG. 8), and the center of each cross-section were determined, the line passing through the center of rotation of the femoral head (described previously with reference to FIG. 5) and passing through an average of the centers of the cross-sections would likely represent the longitudinal axis 845 of the femoral neck 823. In reality, it is difficult to locate the center of each cross-section of the femoral neck 823. It is also difficult to locate the plane at which each cross-section would be taken. Theoretically, each cross-section is located at a plane perpendicular to the longitudinal axis 845, but this presents a somewhat circular method for determining the orientation of the cross-sectional planes and the longitudinal axis 845.

One method for determining the proper orientation of the cross-sectional planes would be to envision an isthmus 849 of the femoral neck 823. The isthmus 849 is the narrowest point on the femoral neck 823 when viewed from the anterior or posterior side of the femur 811. Visualization of the posterior side 831 of the femur 811 allows a lateral line to be constructed across the femoral neck 823 at the isthmus 849. In FIG. 8, the line at section C—C represents an isthmus plane 851, which is a cross-sectional plane extending through the femur in an antero-posterior direction. The visualization of this plane at the isthmus 849 of the femoral neck 823 allows a close approximation of a plane that would be perpendicular to the longitudinal axis 845 of the femur 811. Other cross-sectional planes visualized through the femoral neck 823 would be parallel to the isthmus plane at the isthmus 849.

In practice, the femoral neck 823 is not actually cut at each of the cross-sectional planes discussed above. Rather, the visualization of these planes is helpful in determining, theoretically, where the longitudinal axis 845 of the femoral neck 823 would lie. It would be sufficient to define the longitudinal axis 845 as the line passing through the center of rotation of the femoral head 821 and the center of the femoral neck 823 at the isthmus 849. However, as previously mentioned, it would also be appropriate and perhaps more accurate to define the longitudinal axis 845 as the line passing through the center of rotation of the femoral head 821 and the average of the centers of the femoral neck 823 taken at several cross-sections, all of which are parallel to the isthmus plane 851. It should also be noted that for some patients, the center of rotation of the femoral head may not necessarily coincide with the longitudinal axis 845.

Figure 9:
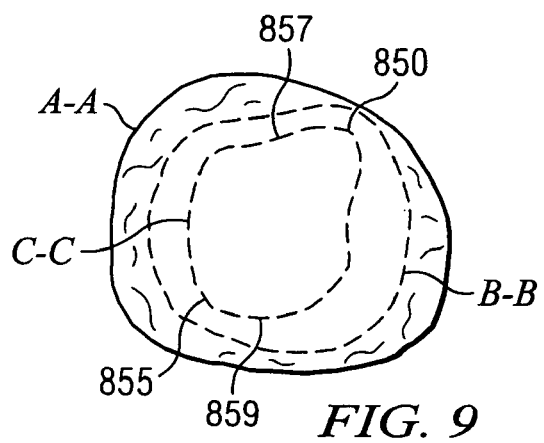
FIG. 9 illustrates multiple cross-sectional views of the femoral head and femoral neck of FIG. 8 taken at A—A, B—B, and C—C.

Referring to FIG. 9, the visualization of the "center" of the femoral neck is not necessarily simple due to the varying geometry of the femoral neck 823. For example, a cross-section taken at A—A in a region of transition between the femoral head 821 and the femoral neck 823 is approximately round. However, the cross-sectional shapes of the femoral neck 823 taken at B—B and C—C are not perfectly round, and instead have various protrusions and other anatomical features that make it difficult to locate the center point of the cross-section. A cross-section from a more proximal portion of the femoral neck 823 is illustrated at B—B and demonstrates that this portion of the neck is somewhat circular in shape. Cross-section C—C at the isthmus 849 of the femoral neck 823 illustrates several prominent features that cause the femoral neck 823 to deviate from a perfectly round shape. The features of the femoral neck at C—C include an antero-superior ridge 850 and a postero-inferior ridge 855. The antero-superior ridge 850 is a pronounced feature of the femoral neck 823 at this part of the femoral neck 823 and joins the greater trochanter 827 in a region distal to the isthmus 849. The postero-inferior ridge 855 is less pronounced and joins the lesser trochanter 829 in a region distal to the isthmus 849. The femoral neck 823 includes a relatively flat superior surface 857, while an inferior surface 859 is more rounded. These anatomical features of any particular femur will vary slightly and could vary greatly from person to person.

Referring still to FIGS. 8 and 9, the center of any given cross-section will be at the mean geometric center for any particular cross-section. When several cross-sections are visualized along the femoral neck 823, the mean geometric centers of all the cross-sections may not be aligned such that the centers can be connected by a line. In this particular instance, a line representing longitudinal axis 845 could be drawn through the center of rotation of the femoral head and through the plurality of cross-sectional centers so as to minimize deviation with respect to the plurality of cross-sectional centers. If the femoral head is misshapen, the longitudinal axis 845 may be considered only with respect to the cross-sectional centers and not the center of rotation of the femoral head.

Alternatively, the center of each cross-section could be located based on the shape of the cancellous bone at that cross-section. Since the prosthesis according to the principles of the present invention is to be implanted within the cancellous bone, it may be more appropriate to define the center of the femoral neck 823 based on the shape and location of the cancellous bone. The center of each cross-section would be the point at which a circle circumscribed around the point would most fully contact the surrounding cortex.

The "location" and/or "visualization" of the longitudinal axis 845 of the femoral neck 823 is theoretical and is discussed to more easily explain how the femoral neck fixation prosthesis is oriented and implanted within the femur 811. It is not necessarily required that the longitudinal axis 845 be found prior to implanting the prosthesis; however, it is important to note that in most cases, the femoral neck fixation prosthesis will be installed in the femur such that a longitudinal axis of the prosthesis is substantially coaxial to the longitudinal axis 845 of the femoral neck 823 as described above. This implantation could be accomplished by using non-invasive techniques such as X-rays or magnetic resonance imaging (MRI) to visualize and locate the longitudinal axis 845 of the femoral head 823, but in most instances, the prosthesis will be implanted using specialized tools that properly orient the prosthesis based on anatomical landmarks on the femoral neck. We believe that the use of these tools and anatomical landmarks will closely align the prosthesis with the longitudinal axis of the femoral neck, thereby obviating the need for calculating or identifying the longitudinal axis during the procedure.

It will be appreciated by those of ordinary skill in the art that certain femoral anatomical variations among patients may result in the prosthesis being implanted such that the longitudinal axis of the prosthesis is not coaxial to the longitudinal axis 845 of the femoral neck 823. In fact, the implantation of the prosthesis in some patients could result in the longitudinal axis of the prosthesis being located as much as 5 to 10 degrees from the longitudinal axis 845 of the femoral neck 823.

Implantation of the femoral neck fixation prosthesis is accomplished by resecting the femoral head 821, reaming at least one passage through the femoral neck, reaming the acetabulum, and implanting the femoral neck fixation prosthesis into the reamed passage. Access to the femoral head and femoral neck is accomplished by making a small incision in the gluteus maximus to expose the hip joint. The femoral head 821 is dislocated from the acetabulum in a manner similar to that employed in current hip arthroplasty procedures. The leg of the patient is then internally rotated (i.e. rotated such that the toe of the patient's foot are rotated toward a medial plane of the body) to expose the femoral head and neck through the incision. Following exposure, the femoral head may be resected as explained below from the internally rotated position. The remaining procedures (i.e. reaming the passages, reaming the acetabulum, and implanting the femoral neck fixation prosthesis) are performed as described below with the patient's leg in either the internally-rotated position or in a neutral position (i.e. non-rotated position). The procedures for preparing the femur and implanting the prosthesis could alternatively be accomplished by rotating the patient's leg externally if the location of the initial incision were moved.

Referring to FIGS. 10–13, a femoral neck clamp 1011 according to principles of the present invention assists in locating the cutting plane at which the femoral head 821 is to be resected. The femoral neck clamp 1011 does this by locating the isthmus 849 of the femoral neck 823 by grasping anatomical landmarks on the femoral neck, such as the antero-superior ridge 850 and the inferior region of the femoral neck 823. Again, the isthmus 849 defines a line that is substantially perpendicular to the longitudinal axis 845 of the femoral neck 823.

Figure 13A:
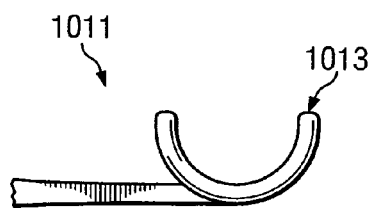
FIG. 13A–13C depict alternative shapes of an inferior clamping member of the femoral neck clamp of FIG. 13.
Figure 13B:
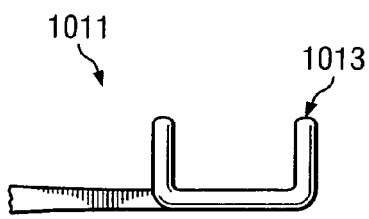
Figure 13:
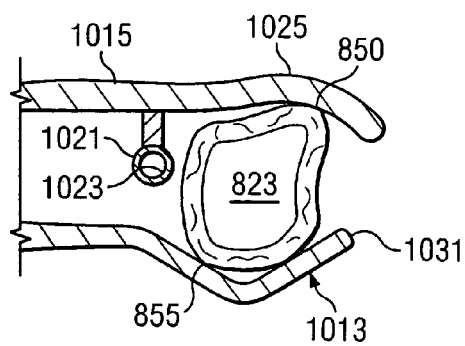
FIG. 13 illustrates a cross-sectional distal view of the femur and femoral neck clamp of FIG. 12 taken at XIII—XIII.
Figure 13C:
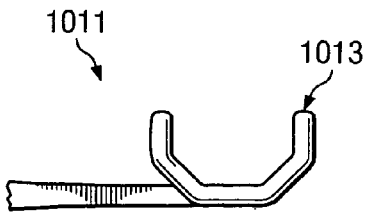

The femoral neck clamp 1011 includes an inferior clamping member 1013 and a superior clamping member 1015. A locator shaft guide member 1021 includes a cylindrical passage 1023 and is attached to either the inferior clamping member 1013 or the superior clamping member 1015. The superior clamping member 1015 preferably includes an arcuate region 1025 for securely gripping the antero-superior ridge 850 (see FIG. 9) of the femoral neck 823; however, the superior clamping member 1015 could be substantially flat with no arcuate region. The inferior clamping member 1013 preferably includes a proximal clasp 1031 and a distal clasp 1033 that are connected by a connecting member 1035. The inferior clamping member 1013 cradles the inferior region of the femoral neck 823 with preferably at least two points of contact occurring between the femoral neck 823 and each of the proximal and distal clasps 1031, 1033. It is important to note that while it is preferred that the shape of the proximal and distal clasps 1031, 1033 is V-shaped, the shape could be hemi-circular (see FIG. 13A), square (see FIG. 13B), polygonal (see FIG. 13C), or any other shape that provides adequate contact with the femoral neck 823. While the preferred embodiment includes the presence of a proximal and distal clasp, the inferior clamping member 1013 may include only one clasp that is preferably aligned with the superior clamping member 1015 to locate the isthmus 849 of the femoral neck 823.

Figure 10:
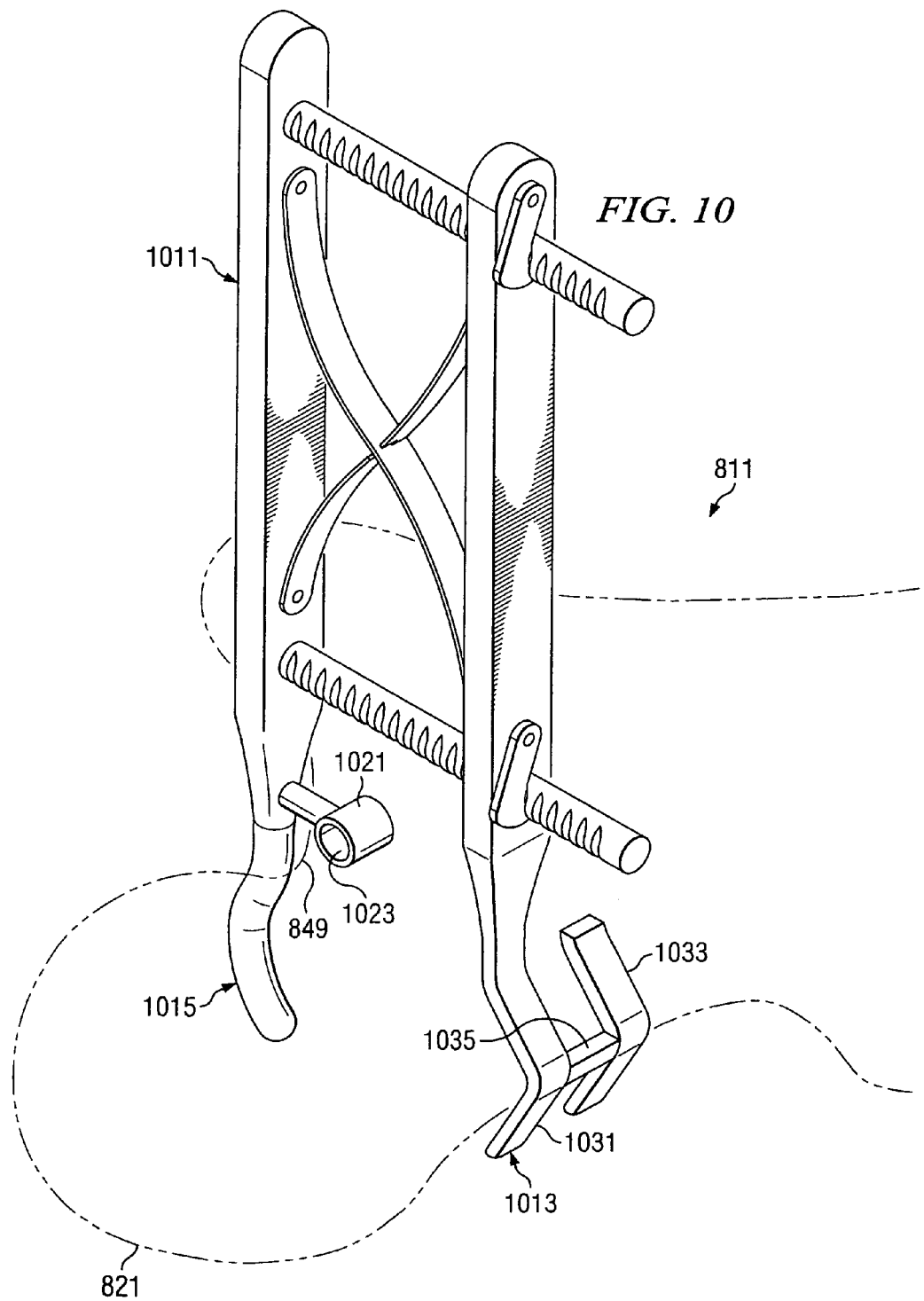
FIG. 10 depicts a perspective view of a femoral neck clamp according to the principles of the present invention positioned at an isthmus of the femoral neck of FIG. 8.
Figure 11:
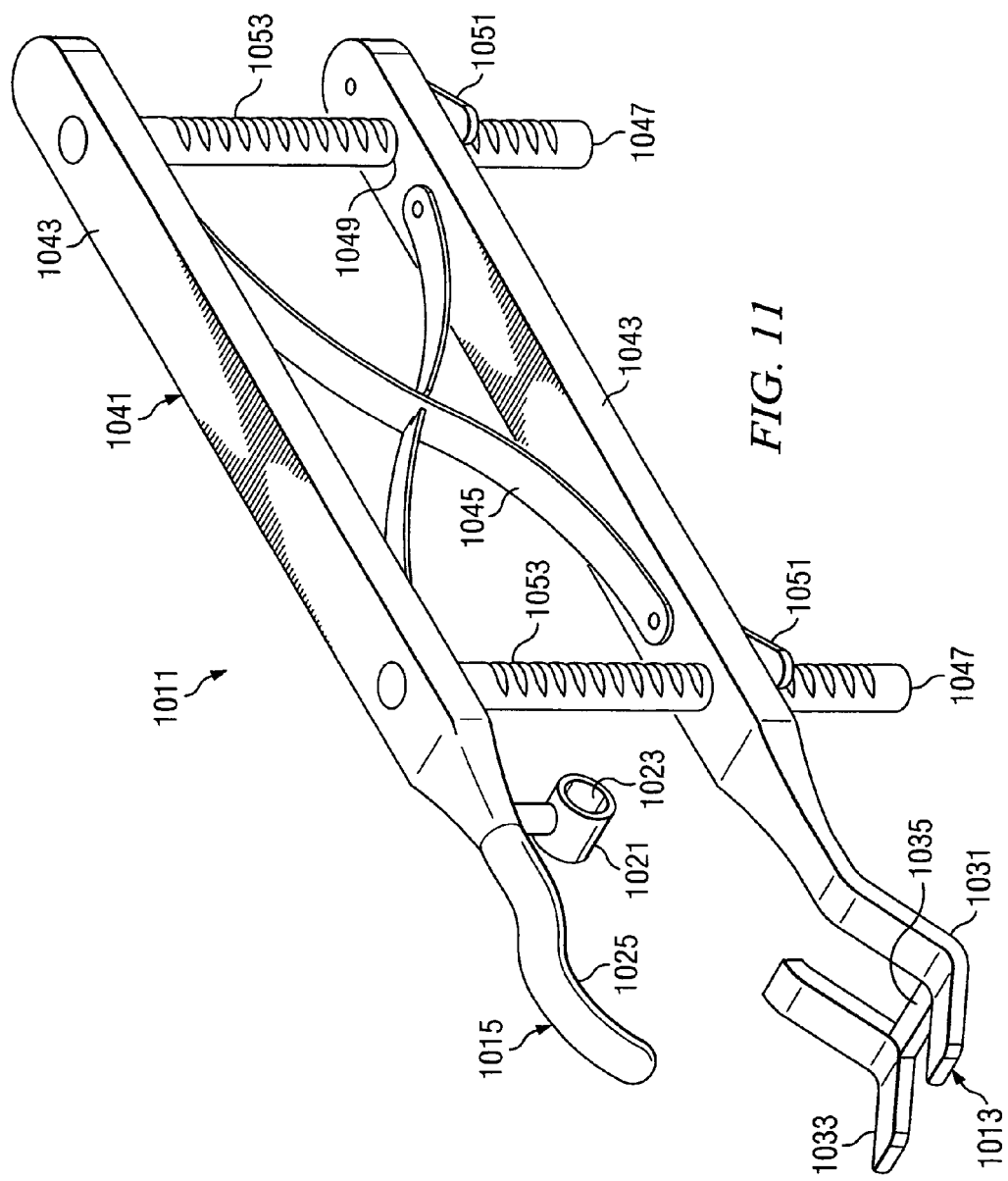
FIG. 11 illustrates a perspective view of the femoral neck clamp of FIG. 10.

Referring still to FIGS. 10 and 11, the femoral neck clamp 1011 preferably includes a handle portion 1041 having a pair of handle members 1043 biased apart by a spring member 1045. The spring member 1045 is preferably made from sheets of spring steel and shaped to hold the handle members 1043 apart in an open position. However, the spring member 1045 could be any device used to apply such a force, including without limitation a helical spring, a leaf spring, or a resilient bushing. A pair of rods 1047 is rigidly attached to one of the handle members, and each rod 1047 passes through an aperture 1049 in the other handle member 1043. Since the handle members 1043 are not pivotally attached, the rods 1047 assist in guiding the movement of the handle members 1043 relative to one another. By applying a force to each handle member 1043 directed toward the other handle members 1043 (i.e. by squeezing the handle members 1043), a surgeon can decrease the distance between the inferior and superior clamping members 1013, 1015 in order to position the clamping members securely around the femoral neck. When the squeezing force applied to the handle members 1043 is released or relaxed, the spring member 1045 pushes the handle members 1043 apart, thereby returning the femoral neck clamp 1011 to the open position. The configuration of the handle members 1043, rods 1047, and spring member 1045 allow the inferior and superior clamping members 1013, 1015 to move in translational, parallel fashion relative to one another when the handle members 1043 are squeezed. Since rotation of the handle members 1043 relative to one another is avoided, the inferior and superior clamping members 1013, 1015 are allowed to more effectively grip the appropriate anatomical features of the femoral neck 823. A locking member 1051 may be attached to the handle portion 1041 to lock the inferior and superior clamping members 1013, 1015 once positioned around the femoral neck 823. The locking member 1051 shown in FIG. 11 is pivotally attached to one of the handle members 1043 and is rotatably positionable to engage a plurality of teeth 1053 on at least one of the rods 1047. In FIG. 11, two locking members 1051 are shown.

Figure 12:
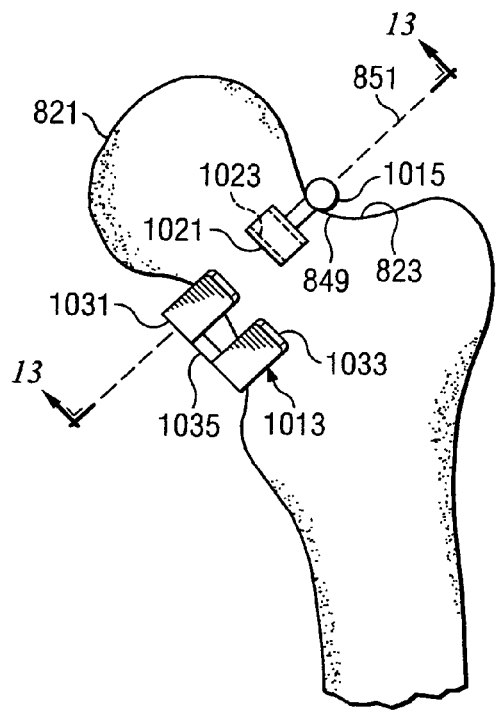
FIG. 12 depicts a posterior view of a human femur with the femoral neck clamp of FIG. 10 shown installed at an isthmus of the femoral neck, the handle members of the femoral neck clamp being omitted for clarity.

The femoral neck clamp 1011 is used to locate the isthmus plane 851, which is represented by a line in FIG. 12 at the isthmus 849 of the femoral neck 823. To find the isthmus plane 851, the inferior and superior clamping members 1013, 1015 are first positioned on inferior and superior sides of the femoral neck 823, respectively, with the superior clamping member 1015 and the proximal clasp 1031 visually aligned with an area of the femoral neck 823 that appears to be the isthmus 849. As the handle members 1043 are squeezed, the superior clamping member 1015 and the proximal clasp 1031 grip the femoral neck 823 in the area of the isthmus 849. Further squeezing of the handle members 1043 and gentle side-to-side manipulation of the femoral neck clamp 1011 in a direction approximately parallel to the longitudinal axis 845 of the femoral neck 823 allows the superior clamping member 1015 and the proximal clasp 1031 to settle at the isthmus 849 of the femoral neck 823. Further alignment of the femoral neck clamp 1011 is ensured by the distal clasp 1033, which prevents the femoral neck clamp 1011 from rotating about the line representing isthmus plane 851 in FIG. 12. The distal clasp 1033 accomplishes this by providing a second point of contact for the inferior clamping member 1013 in the inferior region of the femoral neck 823. Preventing rotation of the femoral neck clamp 1011 about the line representing isthmus plane 851 in FIG. 12 could also be accomplished by having an inferior clamping member 1013 that included a single clasp with a wider area of contact on the inferior region of the femoral neck 823. However, widening either the inferior clamping member 1013 or the superior clamping member 1015 too much will decrease the ability of the femoral neck clamp 1011 to find the isthmus 849 since the inferior and superior clamping members 1013, 1015 will be unable to properly settle into the concave portions of the femoral neck 823 as illustrated in FIG. 12.

Both the inferior and superior clamping members 1013, 1015 take advantage of anatomical landmarks present on the femoral neck 823 to locate the isthmus 849 and the isthmus plane 851, which is typically substantially perpendicular to the longitudinal axis 845 of the femoral neck 823. As previously mentioned, the superior clamping member 1015 primarily contacts and, depending on whether it includes an arcuate region 1025, cradles the antero-superior ridge 850 (see FIG. 13). The inferior clamping member 1013, including the proximal and distal clasps 1031, 1033, preferably is formed in one of the shapes previously described (see FIGS. 13–13C) to cradle the postero-inferior ridge 855 and other portions of the inferior region of the femoral neck 823. The distal clasp 1033 of the inferior clamping member 1013 provides stability to the femoral neck clamp 1011 to prevent rotation of the femoral neck clamp 1011 about the line representing isthmus plane 851 in FIG. 12. The distal clasp 1033 is preferably not directly connected to either handle member 1043, but rather is connected to proximal clasp 1031 by the connecting member 1035, which allows rotation of the distal clasp 1033 relative to the proximal clasp 1031. By connecting the distal clasp 1033 to the proximal clasp 1031 (as opposed to the handle members 1043), the application of force through the handle members 1043 is directed primarily to the superior clamping member 1015 and the proximal clasp 1031. This allows the superior clamping member 1015 and the proximal clasp 1031 to more easily locate the isthmus 849 of the femoral neck 823, while the distal clasp 1033 maintains rotational stability of the femoral neck clamp 1011 without causing the superior clamping member 1015 and the proximal clasp 1031 to shift positions along the femoral neck 823.

Figure 14:
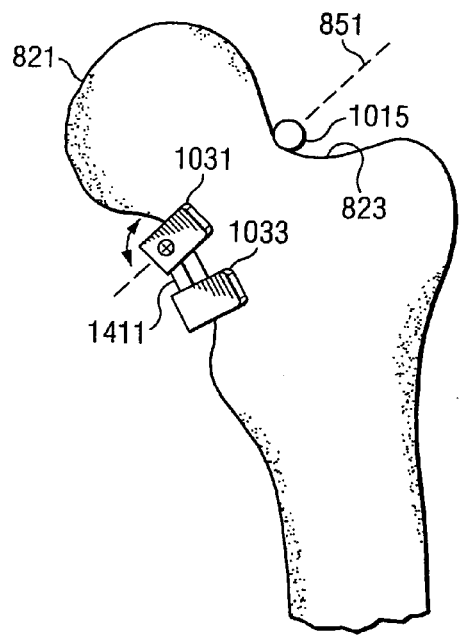
FIG. 14 illustrates a posterior view of the femur and femoral neck clamp having superior and inferior clamping members, the inferior clamping member having a proximal clasp attached to a distal clasp by a connecting member according to principles of the present invention.
Figure 15:
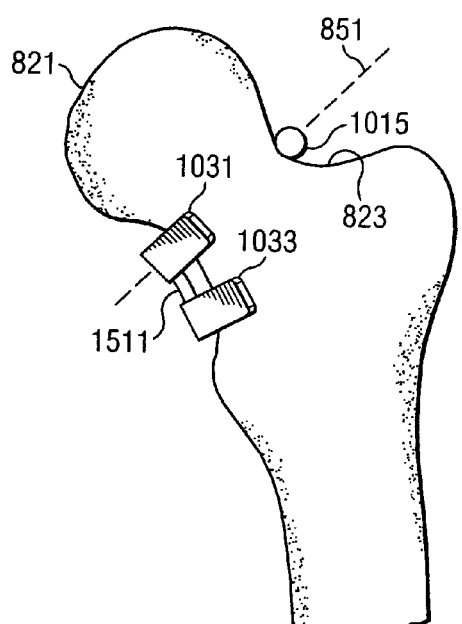
FIG. 15 depicts a posterior view of a femur and femoral neck clamp similar to those of FIG. 14, the femoral neck clamp having an alternative connecting member according to the principles of the present invention.
Figure 16:
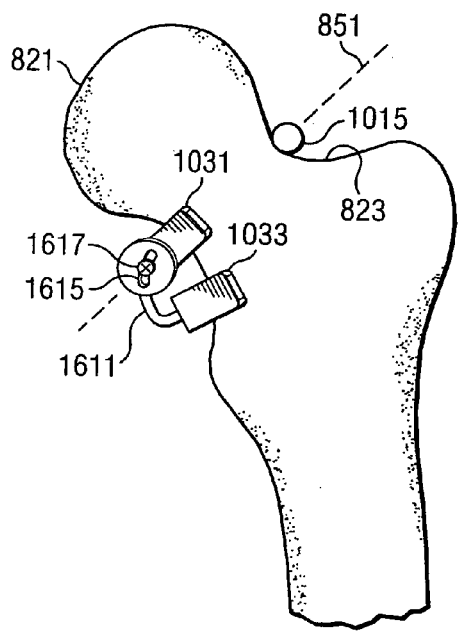
FIG. 16 illustrates a posterior view of a femur and femoral neck clamp similar to those of FIG. 14, the femoral neck clamp having an alternative connecting member according to the principles of the present invention.

Referring to FIGS. 14–16 in the drawings, several different variations of the connecting member 1035 are shown, each of which would be suitable to allow rotation of the distal clasp 1033. In FIG. 14, a connecting member 1411 is rigidly connected to the distal clasp 1033 and pivotally connected to the proximal clasp 1031. A torsion spring (not shown) is operably connected to the proximal clasp 1031 and the connecting member 1411 to bias the distal clasp 1033 toward the femoral neck 823 in a counter-clockwise direction (with respect to the view shown in FIG. 14). In FIG. 15, a connecting member 1511 is rigidly connected to both the proximal and distal clasps 1031, 1033. The connecting member 1511 is preferably made from a resilient material such as spring steel that allows rotation of the distal clasp 1033 relative to the proximal clasp 1031, but provides sufficient force to the distal clasp 1033 to firmly contact the femoral neck 823. In FIG. 16, a connecting member 1611 is rigidly attached to the distal clasp 1033 and is pivotally attached to the proximal clasp 1031. The connecting member includes a slot 1615; and a fastener 1617, preferably a screw, a bolt, or a locking pin, is received through the slot 1615 and is attached to the proximal clasp 1031. The fastener 1617 allows rotation of the distal clasp 1033 to be selectively chosen. After rotating the distal clasp 1033 enough to firmly contact the femoral neck 823, the fastener can be tightened or locked in place to prevent further rotation of the distal clasp 1033 relative to the proximal clasp 1031.

Referring again to FIGS. 10–12, the locator shaft guide member 1021 of the femoral neck clamp 1011 is connected to the superior clamping member 1015 or the handle member 1043 adjacent the superior clamping member 1015. The locator shaft guide member 1021 is oriented such that the cylindrical passage 1023 of the locator shaft guide member 1021 is substantially parallel to the longitudinal axis 845 of the femoral neck 823 when the femoral neck clamp 1011 is finally positioned at the isthmus 849. Typically, the locator shaft guide member 1021 will be rigidly connected to the superior clamping member 1015 because the anatomy of most femurs is such that the positioning of femoral neck clamp 1011 at the isthmus 849 will provide automatic, parallel alignment of the locator shaft guide member 1021 relative to the longitudinal axis 845 of the femoral neck 823. However, it is conceivable that certain anatomical features of some femurs may prevent proper alignment of the locator shaft guide member 1021, so the locator shaft guide member 1021 may be adjustably mounted to the superior clamping member 1015 to allow for rotational adjustment and visual alignment of the locator shaft guide member 1021 relative to the longitudinal axis 845.

Figure 17:
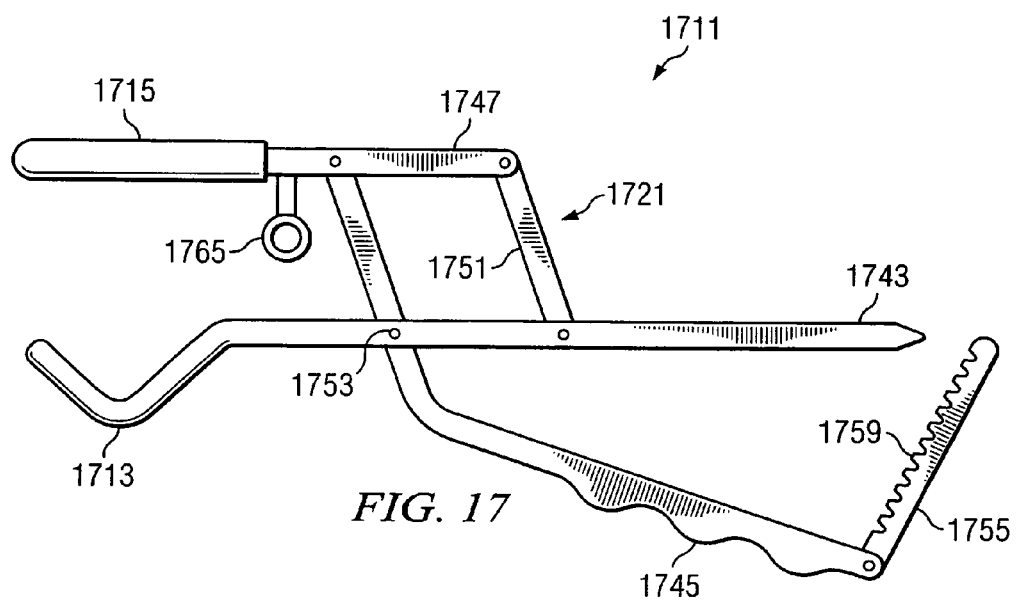
FIG. 17 depicts a side view of a femoral neck clamp according to the principles of the present invention.

Referring to FIG. 17, a femoral neck clamp 1711 according to the principles of the present invention includes an inferior clamping member 1713 and a superior clamping member 1715 similar to those of femoral neck clamp 1011. Femoral neck clamp 1711 includes a parallelogram, four-bar-linkage mechanism 1721 to provide translational movement (as opposed to rotational movement) of the inferior clamping member 1713 relative to the superior clamping member 1715. Linkage mechanism 1721 includes an inferior handle member 1743 pivotally connected to a superior handle member 1745. Superior handle member 1745 is pivotally connected at one end to a coupler link 1747 that is rigidly connected to the superior clamping member 1715. A side link 1751 is pivotally connected at one end to the coupler link 1747 and at another end to the inferior handle member 1743. The side link 1751 and the portion of the superior handle member 1745 extending between the inferior handle member 1743 and the coupler link 1747 are preferably parallel and equal in length. The coupler link 1747 and the portion of the inferior handle member 1743 extending between the superior handle member 1745 and the side link 1751 are preferably parallel and equal in length. A torsion spring 1753, or other spring mechanism, may be operably connected to the inferior handle member 1743 and superior handle member 1745 to bias the handle members 1743, 1745, and thus the inferior and superior clamping members 1713, 1715, apart. A locking member 1755 may be pivotally attached to an end of either the inferior or superior handle members 1743, 1745. Preferably, the locking member 1755 includes a plurality of teeth 1759 adapted to engage the other handle member 1743, 1745 and thus lock the inferior clamping member 1713 relative to the superior clamping member 1715. A locator shaft guide member 1765 is connected to either the inferior clamping member 1713 or the superior clamping member 1715 similar to locator shaft guide member 1021 of FIG. 12. Alternatively, the locator shaft guide member 1765 could be connected to coupler link 1747, inferior handle member 1743, or superior handle member 1745 near the inferior and superior clamping members 1713, 1715.

Figure 18:
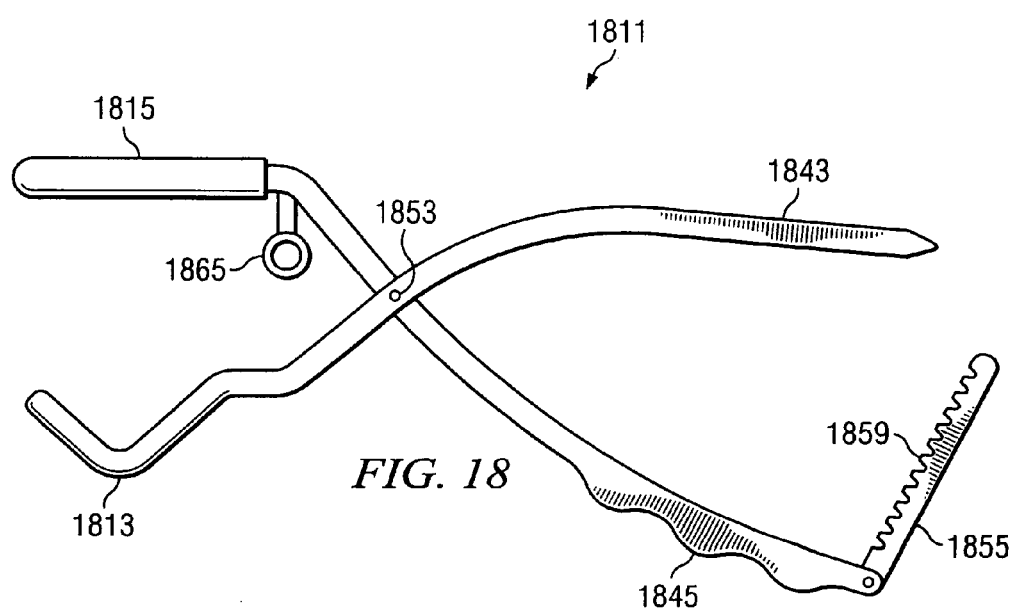
FIG. 18 illustrates a side view of a femoral neck clamp according to the principles of the present invention.

Referring to FIG. 18, a femoral neck clamp 1811 according to the principles of the present invention includes an inferior clamping member 1813 and a superior clamping member 1815 similar to those of femoral neck clamp 1011. Femoral neck clamp 1811 further includes an inferior handle member 1843 pivotally connected to a superior handle member 1845. A torsion spring 1853, or other spring mechanism, may be operably connected to the inferior handle member 1843 and superior handle member 1845 to bias the handle members 1843, 1845, and thus the inferior and superior clamping members 1813, 1815, apart. A locking member 1855 may be pivotally attached to an end of either the inferior or superior handle members 1843, 1845. Preferably, the locking member 1855 includes a plurality of teeth 1859 adapted to engage the other handle member 1843, 1845 and thus lock the inferior clamping member 1813 relative to the superior clamping member 1815. A locator shaft guide member 1865 is connected to either the inferior clamping member 1813 or the superior clamping member 1815 similar to locator shaft guide member 1013 of FIG. 12.

Figure 19:
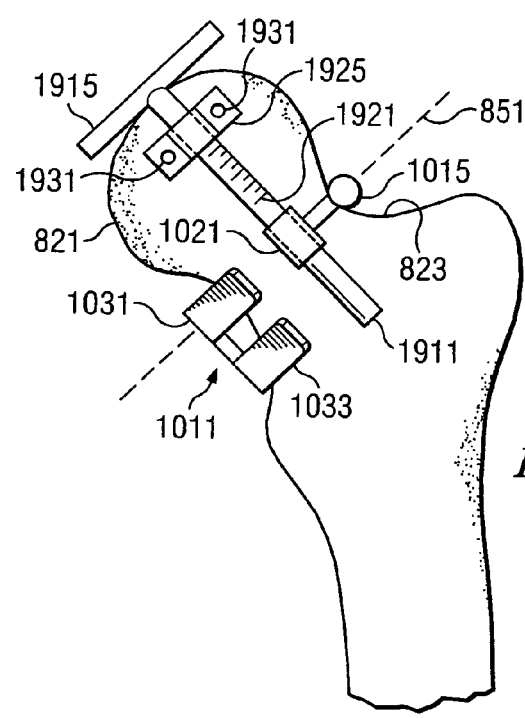
FIG. 19 depicts a posterior view of a human femur having a femoral neck clamp attached to a femoral neck of the femur, a locator shaft connected to the femoral neck clamp, and a pin locator guide slidingly received on the locator shaft.

Referring to FIG. 19, the femoral neck clamp 1011 (could also be femoral neck clamp 1711 or 1811) has been positioned around the femoral neck 823 at the isthmus 849 such that the superior clamping member 1015 and the proximal clasp 1031 of the inferior clamping member 1013 are aligned with the isthmus plane 851. The distal clasp 1033 also engages the femoral neck 823 to prevent rotation of the femoral neck clamp 1011 about the line representing isthmus plane 851. Following positioning of the femoral neck clamp 1011 at the isthmus 849, the locator shaft guide member 1021 is automatically aligned such that a longitudinal axis of the cylindrical passage 1023 of the locator shaft guide member 1021 is oriented at an angle of approximately ninety (90) degrees to the isthmus plane 851.

A locator shaft 1911 is positioned within the cylindrical passage 1023 of the locator shaft guide member 1021 after the femoral neck clamp 1011 has been positioned at the isthmus 849 of the femoral neck 823. A base plate 1915 is rigidly connected to an end of the locator shaft 1911 such that following insertion of the locator shaft 1911 in the cylindrical passage 1023, the locator shaft 1911 can be advanced in a distal/lateral direction until the base plate 1915 abuts the femoral head 821. Indicia 1921 in the form of ruled demarcations is printed along the locator shaft 1911 for accurately positioning a pin locator guide 1925, which is slidingly received on the locator shaft 1911. Pin locator guide 1925 preferably includes at least two spaced apart holes 1931 that may be located on one side of the locator shaft 1911, or as illustrated in FIG. 19, may be located on opposite sides of the locator shaft 1911. Holes 1931 are positioned on the pin locator guide 1925 such that a line connecting the center of the holes 1931 is preferably parallel to the isthmus plane 851.

Figure 20:
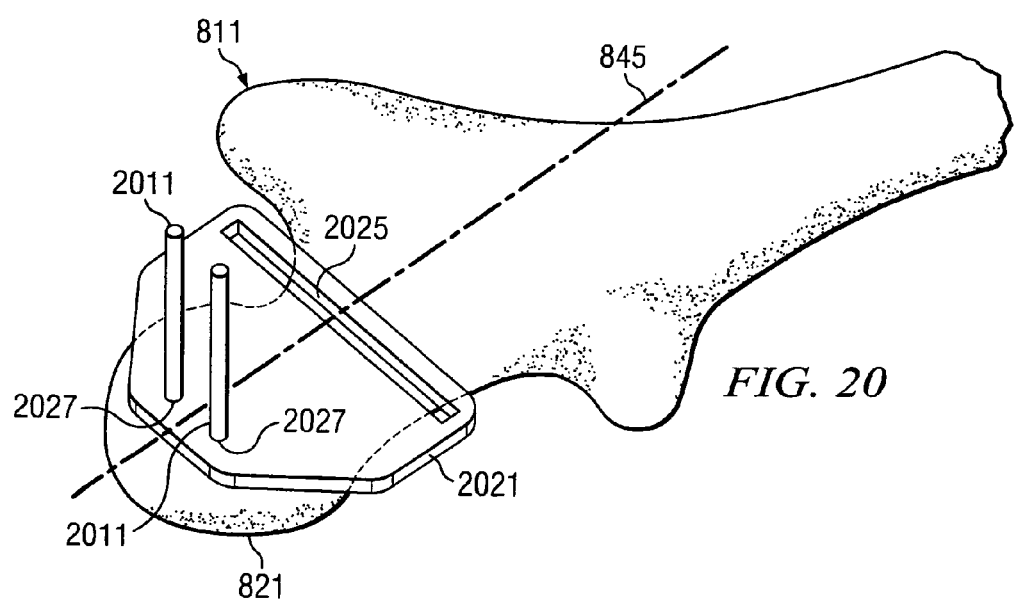
FIG. 20 illustrates a perspective view of a human femur having a cutting guide positioned on pins placed in the femoral head using the pin locator guide of FIG. 19.

Referring to FIGS. 19 and 20, by slidably positioning the pin locator guide 1925 along the locator shaft 1911 a selectable distance from the proximal end of the femoral head 821, pins 2011 can be inserted through the holes 1931 on the pin locator guide 1925. The placement of the pins 2011 in the femoral head 821 fixes the previously determined orientation of the isthmus plane 851, which allows the femoral neck clamp 1011 to be removed from the femur. In FIG. 20, a cutting guide 2021 includes a pair of holes 2027 that are spaced apart the same distance as the holes on the pin locator guide 1925. The cutting guide 2021 is placed over the pins 2011 such that the pins 2011 are received by the holes 2027. A cutting slot 2025 is positioned on the cutting guide 2021 such that it is oriented substantially parallel to a line connecting the centers of the two holes 2027. When installed on the pins 2011 as shown in FIG. 20, the cutting guide 2021 places the cutting slot 2025 a known distance from the pins 2011 to allow resection of the femoral head 821 along a cutting plane (not shown) that is substantially parallel to the isthmus plane 851. The femoral head 821 is resected from the femur 811 by inserting a cutting blade or other cutting tool through the cutting slot 2025 and cutting through that portion of the femur 811.

As mentioned previously, the locator shaft 1911 includes indicia 1921 in the form of ruled demarcations that are spaced apart precise distances. These demarcations can be used to precisely locate the cutting plane relative to the proximal end of the femoral head 821. The amount of resection that will be performed depends on several factors. A prosthetic femoral head will be chosen to match the measured diameter of the patient's native femoral head. This is done to insure that the center of rotation is closely matched by the prosthesis and that the length of the patient's leg is not significantly lengthened or shortened. Based on the diameter chosen for the prosthetic femoral head, a height of the prosthetic femoral head (measured along longitudinal axis 845) will be known. This height equates to the amount of bone resected from the proximal end of the native femoral head 823. Since the distance between the holes 2027 on the cutting guide 2021 and the cutting slot 2025 is known, the pin locator guide 1925 can be accurately positioned along the locator shaft 1911 using the indicia 1921 to place the pin locator guide 1925 according to the amount of bone that needs to be resected. The placement of the pins 2011 using the pin locator guide 1925 then allows the cutting slot 2025 to be accurately positioned at the correct location to remove the correct length of bone.

It will be apparent to one of ordinary skill in the art that the cutting guide 2021 of the present invention could be combined with the femoral neck clamp 1011 to eliminate the need for a locator shaft 1911 and a pin locator guide 1925. The combination clamp and cutting guide would allow the clamp to be positioned at the isthmus 849 of the femoral neck 823 as previously described, but would provide a slot or other guide to allow resection of the femoral head along a cutting plane substantially parallel to the isthmus plane 851. The slot or guide would be adjustable relative to the isthmus plane 851 to allow a measured amount of bone to be resected from the femur 811. A cutting guide that aligns the cutting plane a measured distance from the isthmus plane 851 would be particularly useful in the event that the femoral head is missing, deformed, substantially misshapen, or broken. Measurements could be performed preoperatively using radiographic measurement techniques (e.g. X-ray).

Figure 20A:
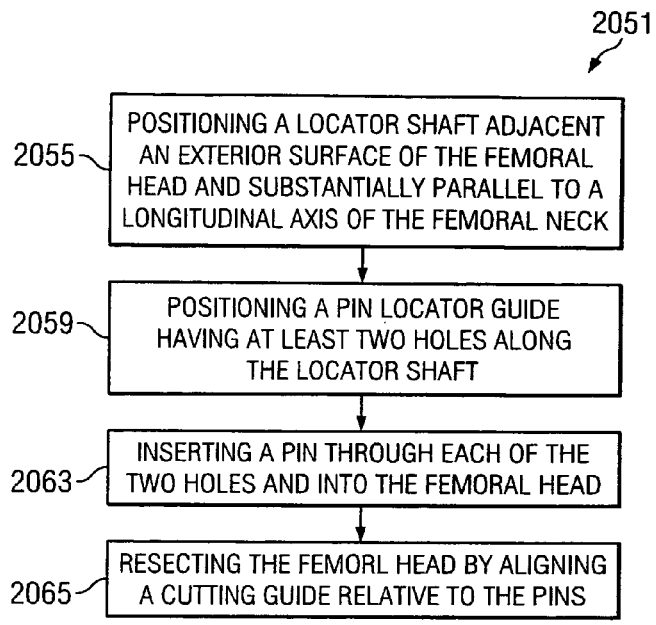
FIG. 20A depicts a method of resecting a femoral head according to the principles of the present invention.

Referring to FIG. 20A, a method of resecting a femoral head from a femur having a femoral neck 2051 is illustrated. The first step at 2055 includes positioning a locator shaft adjacent an exterior surface of the femoral head and substantially parallel to a longitudinal axis of the femoral neck. At step 2059 a pin locator guide having a least two holes is positioned along the locator shaft. At step 2063 a pin is inserted through each of the two holes in the pin locator guide and into the femoral head. The femoral head is resected by aligning a cutting guide relative to the pins at step 2065.

Figure 21:
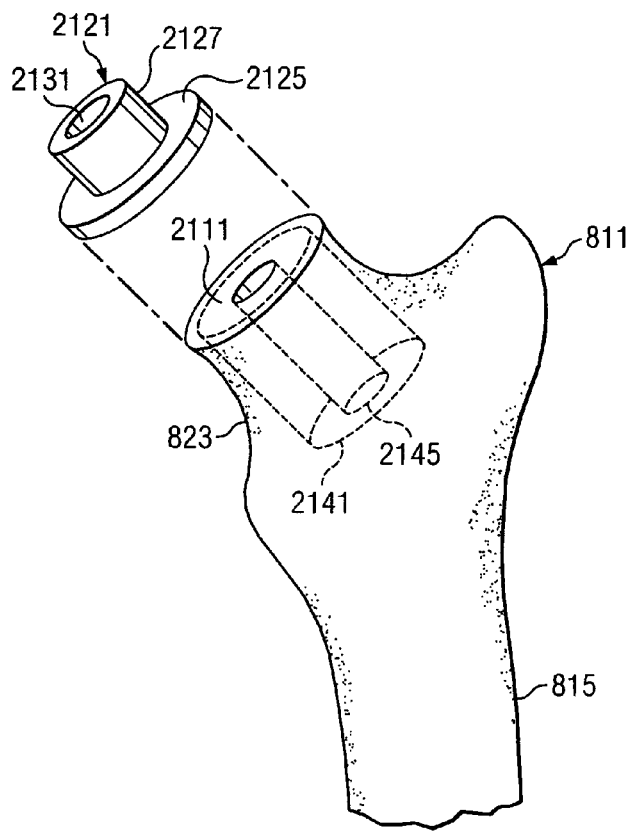
FIG. 21 illustrates a perspective view of a starter guide according to the principles of the present invention and a human femur having the femoral head of the femur resected.

Following resection of the femoral head 821, a proximal neck surface 2111 is exposed that is substantially parallel to the isthmus plane 851. Progressive reaming and drilling of the femoral neck 823 is needed to prepare passages between the proximal neck surface 2111 and the lateral side 815 of the femur 821. With the patient's leg still in an internally rotated position (or alternatively in an externally rotated position), a starter guide 2121 having a positioning portion 2125 and a guide portion 2127 is placed against the proximal neck surface 2111 such that the surface of the positioning portion 2125 opposite the guide portion 2127 mates with the proximal neck surface 2111. The starter guide 2121 further includes a guide passage 2131 that passes through both the guide portion 2127 and the positioning portion 2125 such that a longitudinal axis of the guide passage 2131 is substantially perpendicular to the proximal neck surface 2111 when the starter guide 2121 is placed against the proximal neck surface 2111. A starter passage, or main passage, or primary passage 2141 (represented in FIG. 21 by dashed lines) is formed in the femoral neck 823 from the proximal neck surface 2111 by first drilling a small hole 2145 using a drill bit or other boring tool placed in the guide passage 2131. The starter passage is preferably drilled only partially into the femoral neck, and not through the lateral side 815 of the femur. When placing the starter guide 2121 and drilling the hole 2145, it is preferred to visualize the approximate center of the femoral neck on the proximal neck surface 2111 so that the hole 2145 is approximately centered within the femoral neck 823.

After drilling the hole 2145, the starter guide 2121 is removed from the proximal neck surface 2111, and the femoral neck 823 is progressively reamed until the hole 2145 extends to the cortical bone of the femoral neck 823, thereby forming the starter passage 2141. In practice, depending on the anatomical shape of the patient's femoral neck 823, it may only be possible to form the starter passage 2141 to contact the cortical bone at two points of contact. It is of course preferable to maximize the number of contacts of the cortical bone, and in most instances, it will be possible to contact the cortical bone in at least three locations without significantly decreasing the wall thickness of the cortex in any location. The starter passage 2141 is reamed to a depth that is preferably equal to the longitudinal length of the body 125, 625, 725 (see FIGS. 1, 6 and 7) of the femoral neck prosthesis. The final diameter of the starter passage 2141, which is determined by how much reaming is needed to contact the cortical bone, will be slightly less than the chosen diameter of the body 125, 625, 725 of the prosthesis.

The method for forming the starter passage 2141 described above is largely based on visualization of the center of the femoral neck and formation of a hole 2145. In an alternative embodiment, a guide may be placed flush against the proximal neck surface 2111 to orient a reamer at a ninety (90) degree angle to the proximal neck surface 2111 and center the reamer relative to the longitudinal axis of the femoral neck. The neck is sequentially reamed until the starter passage 2141 extends to the cortex. In another embodiment, a guide pin may be inserted into the femoral neck substantially parallel to the longitudinal axis of the femoral neck. The pin may be placed based on visualization or guided into place with a guide that is fixed relative to the femoral neck. The guide pin would be used to direct sequential reaming of the starter passage 2141.

Figure 22:
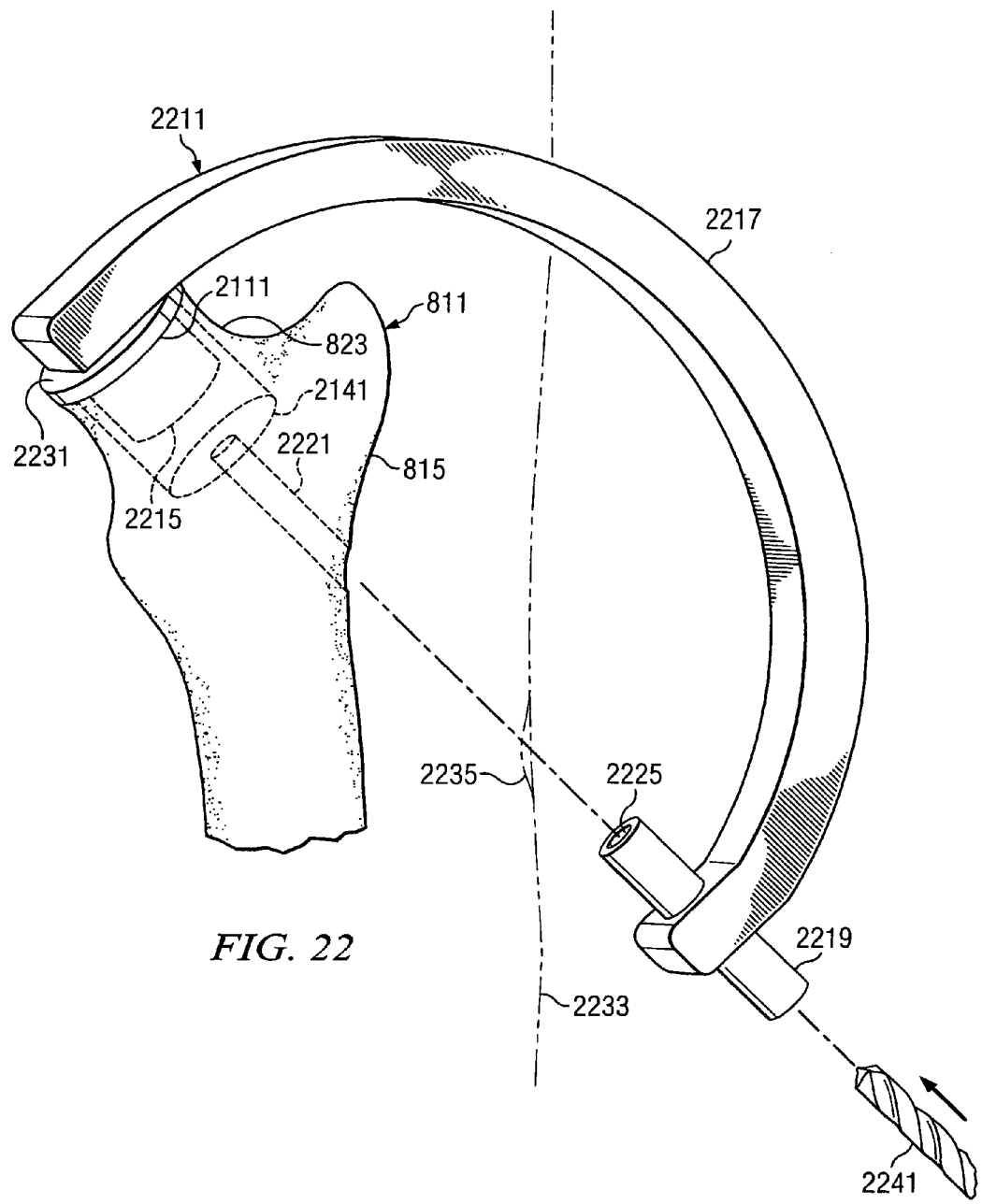
FIG. 22 depicts a posterior view of a human leg, including a human femur, and a drilling guide according to the principles of the present invention for preparing the femur for implantation of a femoral neck prosthesis.
Figure 23:
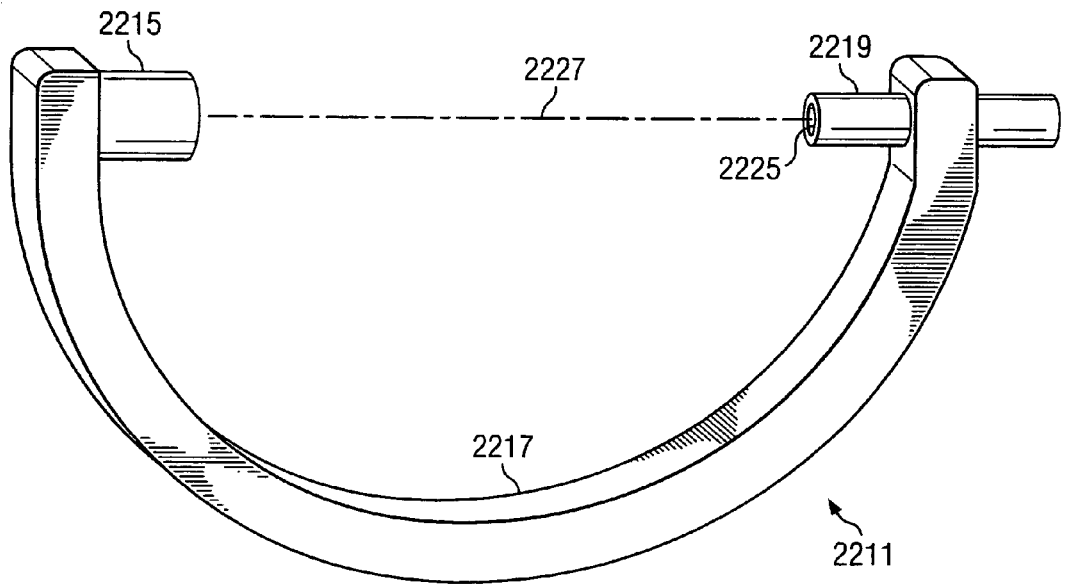
FIG. 23 illustrates a side view of the drilling guide of FIG. 22.

Referring to FIGS. 22 and 23, a drilling guide 2211 having an anchor member 2215 rigidly connected by a connecting member 2217 to an alignment sleeve 2219 is used to drill a distal passage, or fastener passage, or secondary passage 2221 (represented in FIG. 22 by dashed lines) from the lateral side 815 of the femur 811. The alignment sleeve 2219 includes an alignment passage 2225 for receiving a drill bit or other boring tool. The connecting member 2217 may be C-shaped and connects the anchor member 2215 to the alignment sleeve 2219 such that a longitudinal axis of the alignment passage 2225 is coaxial to the longitudinal axis of the anchor member 2215, both of which are coaxial to a longitudinal axis 2227 of the drilling guide 2211. The anchor member 2215 is cylindrical and sized to fit within the starter passage 2141. The anchor member 2215 could be interchangeable to allow different diameters to be used to properly fit within the starter passage 2141 of a particular patient. Alternatively, the anchor member 2215 could be tapered to allow a snug fit within starter passages 2141 of several different diameters. The anchor member 2215 may also include a collar 2231 for further stabilizing the drilling guide 2211 against the proximal neck surface 2111 when inserted into the starter passage 2141.

After positioning the anchor member 2215 within the starter passage 2141, the alignment sleeve 2219 is located on the lateral side 815 of the femur 811. The patient's skin and other soft tissue 2233 are located between the alignment sleeve 2219 and the femur 821. The leg of the patient is then rotated to a neutral position, and an incision 2235 is made through the soft tissue of the patient in the vicinity of the alignment sleeve 2219. A drilling bit 2241 or other boring tool is inserted through the alignment passage 2225 of the alignment sleeve 2219 for drilling the distal passage 2221 to join the starter passage 2141. Because the alignment sleeve 2219 is coaxial to the anchor member 2215 and because the anchor member 2215 is securely positioned within the starter passage 2141, the distal passage 2221 is easily formed coaxial to the starter passage 2221. As shown in FIG. 22, the distal passage 2221 is typically smaller in diameter than the starter passage 2141, since the distal passage 2221 will receive the fastener 120, 620, 720 (see FIGS. 1, 6, and 7) for securing to the body 126, 625, 725 of the femoral neck fixation prosthesis.

The primary reason for using a drilling guide 2211 to complete drilling through the femur is that it is less desirable to drill a hole completely through the femur from the proximal neck surface 2111 toward the lateral side 815 of the femur 811. When drilling from the proximal neck surface 2111, the patient's leg would be in the internally rotated position. It is not as safe to drill through the lateral side 815 of the femur 811 when the leg is internally rotated because the drill bit may contact and sever vital anatomy, such as the femoral artery or other vessels and nerves, upon exiting the femur 811. Since use of the drilling guide 2211 allows the leg to be rotated back to the neutral position, drilling can proceed from the lateral side 815 of the femur 811 without fear of contacting vital anatomy.

Figure 23A:
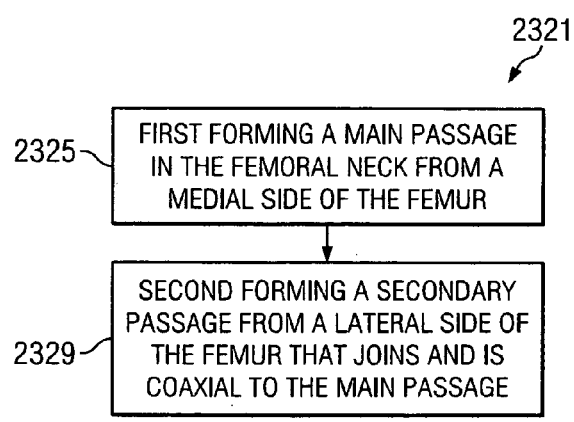
FIG. 23A depicts a method of preparing a femur for implantation of a prosthesis according to the principles of the present invention.

Referring to FIG. 23A, a method of preparing a femur for implantation of a femoral neck fixation prosthesis 2321 includes two steps. The first step at 2325 includes first forming a main passage in the femoral neck from a medial side of the femur substantially coaxial to a longitudinal axis of a femoral neck. The second step at 2329 includes second forming a secondary passage from a lateral side of the femur that is coaxial to and joins the main passage.

Although the preparation of the femur for implantation of the prosthesis includes forming two separate passages from different sides of the femur, the starter and distal passages could be formed from the same side of the femur. Following the formation of the starter passage 2141, a guide may be placed within the starter passage 2141 to guide drilling of the distal passage 2221 from the proximal side of the femoral neck 823. Since the leg of the patient would likely be in an internally rotated position during this drilling procedure, care would be taken to only slightly penetrate the cortex on the lateral side of the femur 821. This would help avoid major arteries and nerves in the patient's leg. After forming both the starter and distal passages 2141, 2221 from the medial side of the femur, the drilling guide 2211 could be used to place the fastener 120, 620, 720 in the femur during the implantation of the femoral neck prosthesis, which is described in more detail below.

After forming both the starter passage 2141 and the distal passage 2221, the femur 811 is capable of receiving the femoral neck fixation prosthesis. However, prior to implantation of the prosthesis, it may be desirable to prepare the acetabulum for receipt of an acetabular component (not shown) that will mate with the head of the femoral neck fixation prosthesis. The starter and distal passages 2141, 2221 may be used to guide the preparation of the acetabulum, which initially involves reaming.

Figure 24:
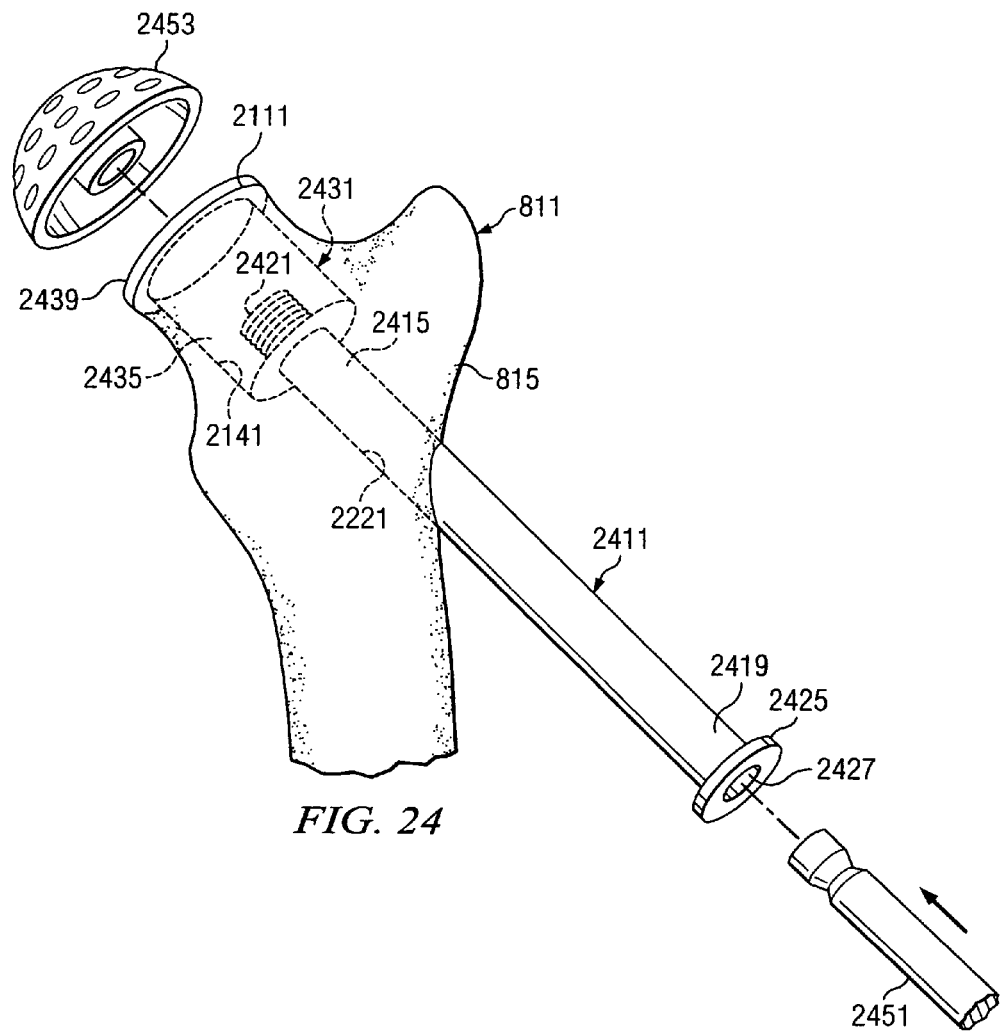
FIG. 24 illustrates a posterior view of a femoral neck liner and a reamer path protector according to the principles of the present invention, the femoral neck liner being positioned within a femoral neck, and the reamer path protector being threadingly received by the femoral neck liner.
Figure 25:
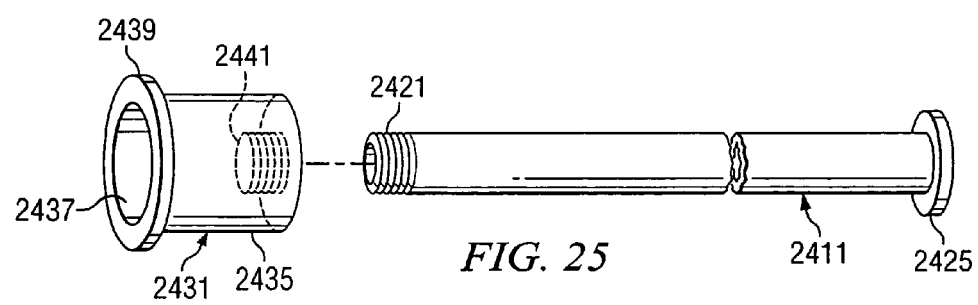
FIG. 25 depicts a side view of the reamer path protector and femoral neck liner of FIG. 23.

Referring to FIGS. 24 and 25, a reamer path protector 2411 includes an insertion end 2415 and a handle end 2419. The insertion end preferably includes a plurality of threads 2421, while the handle end 2419 includes a hand guard 2425. A passage 2427 passes through the reamer path protector 2411. A femoral neck liner 2431 is also provided and includes a main body 2435 having a passage 2437 and a collar 2439. The passage 2437 includes internal threads 2441 at an end of the main body 2335 opposite collar 2339.

In operation, the reamer path protector 2411 is inserted from the lateral side 815 of the femur 811 and into the distal passage 2221. The femoral neck liner 2431 is inserted from the proximal neck surface 2111 into the starter passage 2141 until the collar 2439 mates with the proximal neck surface 2111. The femoral neck liner 2431 is sized in diameter the same as or slightly less than the diameter of the starter passage 2141. As is the case with the anchor member 2215 (see FIG. 22) discussed previously, the femoral neck liner 2431 could be provided in different sizes to fit variously sized starter passages 2141, or the femoral neck liner 2431 could be tapered. After inserting the femoral neck liner 2431, the reamer path protector 2411 is advanced further into the distal passage 2221 until it contacts the femoral neck liner 2431. The reamer path protector 2411 is then rotated to engage the threads 2421 with internal threads 2441. The attachment mechanism between the reamer path protector 2411 and the femoral neck liner 2431 is not required to be accomplished by a threaded connection. The connection could be formed by any mechanism that would allow the components to be easily disassembled following reaming of the acetabulum.

When the reamer path protector 2411 is securely fastened to the femoral neck liner 2431, a sufficient portion of the reamer path protector 2411 remains extending outside of the femur 811 to allow gripping by the surgeon or other person who will ream the acetabulum. The reamer path protector 2411 is therefore gripped in this area, and a reamer shaft 2451 is inserted through the passage 2427 and the passage 2437 to connect to a reamer head 2453 near the proximal neck surface 2111. The acetabulum is then reamed by rotating the patient's leg into a neutral position and applying power to rotate the reamer shaft 2451 and reamer head 2453 from the lateral side 815 of the femur 811. Some internal rotation of the femur 811 may also be necessary depending on the position of the femur 811 relative to flexion/extension and abduction/adduction. The acetabulum is progressively reamed until enough material has been removed to accommodate the acetabular component of the prosthesis. By reaming the acetabulum through the distal and starter passages 2221, 2141 formed in the femur 811, a highly effective reaming process is accomplished. Since the patient's leg is positioned in the neutral position during the reaming process, and since the reamer head 2353 is connected to the reamer shaft 2451 along the same axis as that about which the head and body of the prosthesis will be oriented, the acetabulum can be efficiently reamed to closely match the shape of the head of the prosthesis.

Following the reaming process, the reamer head 2453 is removed from the reamer shaft 2451, and the reamer shaft 2451 is removed from the femoral neck liner 2431 and the reamer path protector 2411. An impactor shaft (not shown) may be inserted into the reamer path protector 2411 and the femoral neck liner 2431 similar to the original insertion of the reamer shaft 2451. The impactor shaft is releasably connected to an impactor head (not shown) near the proximal neck surface 2111. The impactor shaft and impactor head are used to apply force to and seat the acetabular component of the prosthesis in the reamed acetabulum. After the acetabular component is firmly seated, the impactor shaft, impactor head, femoral neck liner 2431, and the reamer path protector 2411 are disassembled and removed from the femur 811

Figure 25A:
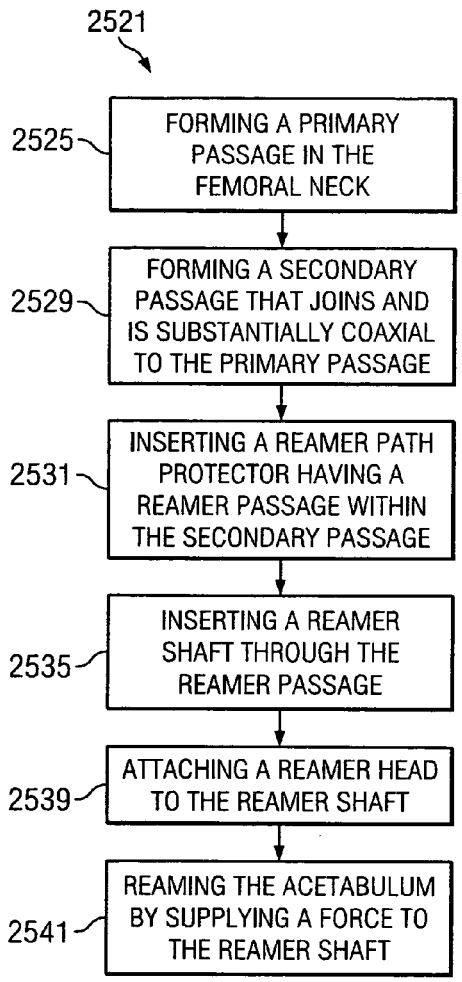
FIG. 25A illustrates a method of preparing an acetabulum according to the principles of the present invention.

Referring to FIG. 25A, a method for preparing an acetabulum for receiving a head of a femoral prosthesis 2521 is illustrated. A first step 2525 includes forming a primary passage within the femur substantially coaxial to a longitudinal axis of the femoral neck. At step 2529, a secondary passage is formed from a lateral side of the femur that joins and is coaxial to the primary passage. Step 2531 includes inserting a reamer path protector having a reamer passage within the secondary passage. A reamer shaft is inserted through the reamer passage at step 2535. A reamer head is attached to the reamer shaft at step 2539, and the acetabulum is reamed at step 2541.

The femoral neck fixation prosthesis is implanted into the femur 811 by inserting the body 125, 625, 725 of the prosthesis into the starter passage 2141. Preferably, the diameter of the body 125, 625, 725 is sized slightly larger than the diameter of the starter passage 2141 such that a secure fit within the starter passage 2141 is obtained when the body 125, 625, 725 is driven into the starter passage 2141. The starter passage 2141 is deep enough to accommodate the body 125, 625, 725 of the prosthesis and allow the collar of the body 125, 625, 725 to mate with the proximal neck surface 2111.

The fastener 120, 620, 720 is then inserted into the distal passage 2221 from the lateral side 815 of the femur 811. To properly feed the fastener 120, 620, 720 through the soft tissue 2233 (see FIG. 22) of the patient's leg and into the distal passage 2221, a small diameter pin can be used to locate and mark the passage when the leg is in the neutral position. The fastener 120, 620, 720, which may be canullated (i.e. having a passage down the center of the shaft), can then be placed onto the pin and fed into the distal passage 2221. The fastener 120, 620, 720 is advanced into the distal passage 2221 until it contacts the body 125, 625, 725 of the prosthesis, at which time the fastener 120, 620, 720 is threadingly connected to the body 125, 625, 725 to secure the body within the femur 811. The head 110, 610, 710 of the prosthesis is then installed on the morse taper 115, 615, 760 of the prosthesis be impacting the head of the prosthesis.

Figure 26:
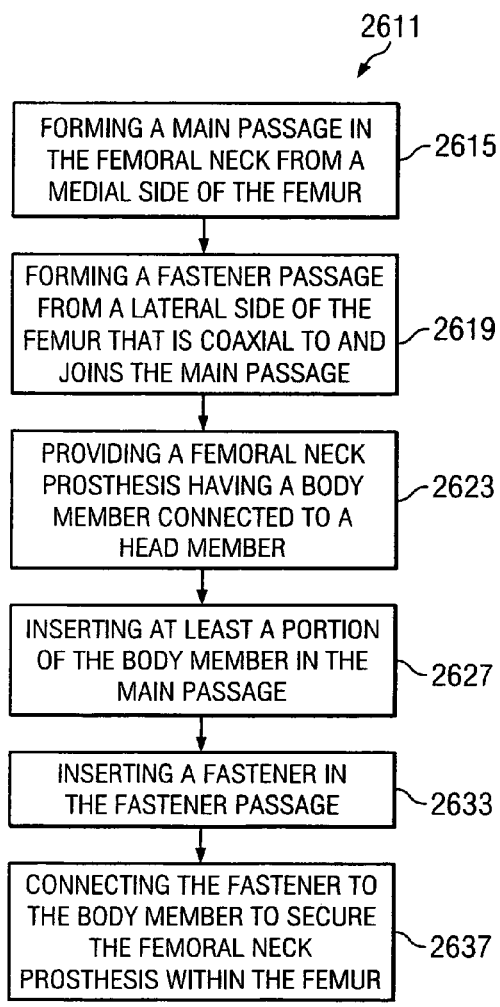
FIG. 26 depicts a method of implanting a prosthesis in a femur according to the principles of the present invention.

Referring to FIG. 26, a method of implanting a prosthesis in a femur 2611 according the principles of the present invention is illustrated. At step 2615 a main passage is formed in the femoral neck from a medial side of the femur substantially coaxial to a longitudinal axis of the femoral neck. At step 2619 a fastener passage is formed from a lateral side of the femur that is coaxial to and joins the main passage. Step 2623 includes providing a femoral neck prosthesis having a body member connected to a head member. At step 2627 a portion of the body member is inserted in the main passage. A fastener is inserted into the fastener passage at step 2633. At step 2637 the fastener is connected to the body member to secure the femoral neck prosthesis within the femur.

As will be recognized by those skilled in the art, the innovative concepts described in the present application can be modified and varied over a tremendous range of applications, and accordingly the scope of patented subject matter is not limited by any of the specific exemplary teachings given.

While the invention has been particularly shown and described with reference to a preferred embodiment, it will be understood by those skilled in the art that various changes in form and detail may be made therein without departing from the spirit and scope of the invention.

The invention claimed is:

1. A method of preparing an acetabulum for receiving a head of a femoral prosthesis, the method comprising:
    forming a primary passage within the femur that is substantially coaxial to a longitudinal axis of a femoral neck;
    forming a secondary passage within the femur that joins and is substantially coaxial to the primary passage;
    inserting a femoral neck liner having a liner passage within the primary passage;
    inserting a reamer path protector having a reamer passage within the secondary passage;
    releasably connecting the reamer path protector to the femoral neck liner such that the reamer passage is substantially aligned with the liner passage;
    inserting a reamer shaft through the reamer passage;
    attaching a reamer head to the reamer shaft;
    reaming the acetabulum by supplying a reaming force to the reamer shaft; and
    wherein the reamer shaft is inserted through the reamer passage and the liner passage prior to attaching the reamer head.

2. A method according to claim 1, wherein the reaming force is applied at an end of the reamer shaft opposite that of the reamer head.

3. A method according to claim 1, further comprising the step of placing the femur in a neutral position during the reaming of the acetabulum.

4. A method according to claim 1, further comprising the steps of:
    removing the reamer shaft from the reamer passage;
    inserting an impactor shaft through the reamer passage;
    connecting an impactor head to the impactor shaft;
    seating an acetabular portion of the femoral prosthesis in the reamed acetabulum by
        supplying an impact force to the impactor shaft to drive the impactor head against the acetabular portion.

* * * * *